US011986517B2

(12) United States Patent
Yan et al.

(10) Patent No.: US 11,986,517 B2
(45) Date of Patent: May 21, 2024

(54) CANCER VACCINES TARGETING MESOTHELIN AND USES THEREOF

(71) Applicant: Inovio Pharmaceuticals, Inc., Plymouth Meeting, PA (US)

(72) Inventors: Jian Yan, Wallingford, PA (US); Anna Slager, Lansdale, PA (US); Bradley Garman, Glenside, PA (US); Neil Cooch, Oreland, PA (US)

(73) Assignee: Inovio Pharmaceuticals, Inc., Plymouth Meeting, PA (US)

( * ) Notice: Subject to any disclaimer, the term of this patent is extended or adjusted under 35 U.S.C. 154(b) by 212 days.

(21) Appl. No.: 17/467,728

(22) Filed: Sep. 7, 2021

(65) Prior Publication Data

US 2021/0401959 A1 Dec. 30, 2021

Related U.S. Application Data

(62) Division of application No. 16/219,287, filed on Dec. 13, 2018, now Pat. No. 11,154,602.

(60) Provisional application No. 62/598,289, filed on Dec. 13, 2017.

(51) Int. Cl.
*A61K 39/39* (2006.01)
*A61K 39/00* (2006.01)
*A61P 35/00* (2006.01)

(52) U.S. Cl.
CPC ...... *A61K 39/001168* (2018.08); *A61K 39/39* (2013.01); *A61P 35/00* (2018.01); *A61K 2039/53* (2013.01); *A61K 2039/55527* (2013.01); *A61K 2039/55538* (2013.01)

(58) Field of Classification Search
CPC ............ A61K 39/001168; A61K 39/39; A61K 2039/55538; A61P 35/00
USPC ...................................................... 424/185.1
See application file for complete search history.

(56) References Cited

U.S. PATENT DOCUMENTS

| | | |
|---|---|---|
| 4,510,245 A | 4/1985 | Cousens et al. |
| 4,554,101 A | 11/1985 | Hopp |
| 4,722,848 A | 2/1988 | Paoletti et al. |
| 4,790,987 A | 12/1988 | Compans et al. |
| 4,797,368 A | 1/1989 | Carter et al. |
| 4,920,209 A | 4/1990 | Davis et al. |
| 4,945,050 A | 7/1990 | Sanford et al. |
| 5,017,487 A | 5/1991 | Stunnenberg et al. |
| 5,036,006 A | 7/1991 | Sanford et al. |
| 5,077,044 A | 12/1991 | Stocker |
| 5,110,587 A | 5/1992 | Paoletti et al. |
| 5,112,749 A | 5/1992 | Brey et al. |
| 5,174,993 A | 12/1992 | Paoletti |
| 5,223,424 A | 6/1993 | Cochran et al. |
| 5,225,336 A | 7/1993 | Paoletti |
| 5,240,703 A | 8/1993 | Cochran |
| 5,242,829 A | 9/1993 | Panicali et al. |
| 5,273,525 A | 12/1993 | Hofmann |
| 5,294,441 A | 3/1994 | Curtiss, III |
| 5,294,548 A | 3/1994 | McLinden et al. |
| 5,310,668 A | 5/1994 | Ellis et al. |
| 5,387,744 A | 2/1995 | Curtiss et al. |
| 5,389,368 A | 2/1995 | Curtiss, III |
| 5,424,065 A | 6/1995 | Curtiss et al. |
| 5,451,499 A | 9/1995 | Cochran |
| 5,453,364 A | 9/1995 | Paoletti |
| 5,462,734 A | 10/1995 | Letchworth et al. |
| 5,470,734 A | 11/1995 | Sondermeijer et al. |
| 5,474,935 A | 12/1995 | Chatterjee et al. |
| 5,482,713 A | 1/1996 | Paoletti |
| 5,580,859 A | 12/1996 | Felgner et al. |
| 5,591,439 A | 1/1997 | Plotkin et al. |
| 5,593,972 A | 1/1997 | Weiner et al. |
| 5,643,579 A | 7/1997 | Hung et al. |
| 5,650,309 A | 7/1997 | Wong-Staal et al. |
| 5,676,594 A | 10/1997 | Joosten |
| 5,698,202 A | 12/1997 | Ertl et al. |
| 5,703,055 A | 12/1997 | Felgner et al. |
| 5,739,118 A | 4/1998 | Carrano et al. |
| 5,817,637 A | 10/1998 | Weiner et al. |
| 5,830,876 A | 11/1998 | Weiner et al. |
| 5,955,088 A | 9/1999 | Ghiasi et al. |
| 5,962,428 A | 10/1999 | Carrano et al. |
| 5,981,505 A | 11/1999 | Weiner et al. |
| 6,034,298 A | 3/2000 | Lam et al. |
| 6,042,836 A | 3/2000 | Berman et al. |

(Continued)

FOREIGN PATENT DOCUMENTS

| | | |
|---|---|---|
| CN | 106061500 A | 10/2016 |
| EP | 1991263 B1 | 12/2014 |

(Continued)

OTHER PUBLICATIONS

Andre et al., "Increased Immune Response Elicited by DNA Vaccination with a Synthetic gp120 Sequence with Optimized Codon Usage" Journal of Virology, vol. 72, No. 2, Feb. 1998, pp. 1497-1503.

Chang et al.; "Mesothelin-specific cell-based vaccine generates antigen-specific immunity and potent antitumor effects by combining with IL-12 immunomodulator"; Gene Therapy; vol. 23; 2016; p. 38-49.

Demi et al., "Multiple Effects of Codon Usage Optimization on Expression and Immunogenicity of DNA Candidate /accines Encoding the Human Immunodeficiency Virus Type 1 Gag Protein" Journal of Virology, vol. 75, No. 22, Nov. 2001, pp. 10991-11001.

(Continued)

*Primary Examiner* — Yan Xiao
(74) *Attorney, Agent, or Firm* — BakerHostetler

(57) ABSTRACT

Disclosed herein are nucleic acid molecules comprising one or more nucleic acid sequences that encode a modified consensus mesothelin antigen. Vectors, compositions, and vaccines comprising one or more nucleic acid sequences that encode a modified consensus mesothelin antigen are disclosed. Methods of treating a subject with a mesothelin-expressing tumor and methods of preventing a mesothelin-expressing tumor are disclosed. Modified consensus mesothelin antigen is disclosed.

3 Claims, 13 Drawing Sheets

Specification includes a Sequence Listing.

(56) References Cited

U.S. PATENT DOCUMENTS

| | | | |
|---|---|---|---|
| 6,110,161 | A | 8/2000 | Mathiesen et al. |
| 6,156,319 | A | 12/2000 | Cohen et al. |
| 6,261,281 | B1 | 7/2001 | Mathiesen et al. |
| 6,589,529 | B1 | 7/2003 | Choi et al. |
| 6,697,669 | B2 | 2/2004 | Dev et al. |
| 6,939,862 | B2 | 9/2005 | Bureau et al. |
| 6,958,060 | B2 | 10/2005 | Mathiesen et al. |
| 7,238,522 | B2 | 7/2007 | Hebel et al. |
| 7,245,963 | B2 | 7/2007 | Draghia-Akli et al. |
| 7,328,064 | B2 | 2/2008 | Mathiesen et al. |
| 8,008,265 | B2 | 8/2011 | Weiner et al. |
| 8,119,395 | B1 | 2/2012 | Weiner et al. |
| 8,173,786 | B2 | 5/2012 | Weiner et al. |
| 8,178,660 | B2 | 5/2012 | Weiner et al. |
| 9,452,285 | B2 | 9/2016 | Draghia-Akli et al. |
| 10,071,154 | B2 | 9/2018 | Weiner et al. |
| 2004/0175727 | A1 | 9/2004 | Draghia-Akli et al. |
| 2005/0005263 | A1 | 1/2005 | Miyazaki |
| 2005/0052630 | A1 | 3/2005 | Smith et al. |
| 2007/0207170 | A1 | 9/2007 | Dubensky et al. |
| 2008/0274140 | A1 | 11/2008 | Weiner et al. |
| 2009/0004716 | A1 | 1/2009 | Draghia-Akli et al. |
| 2012/0076752 | A1 | 3/2012 | Wu et al. |
| 2013/0315950 | A1 | 11/2013 | Dubensky et al. |
| 2014/0010861 | A1 | 1/2014 | Bancel et al. |
| 2014/0154248 | A1 | 6/2014 | Pastan et al. |
| 2016/0030536 | A1 | 2/2016 | Weiner et al. |
| 2016/0317634 | A1 | 11/2016 | Springer et al. |

FOREIGN PATENT DOCUMENTS

| | | |
|---|---|---|
| JP | 2009-528065 A | 8/2009 |
| JP | 2013-530155 A | 7/2013 |
| JP | 2016-516723 A | 6/2016 |
| JP | 2017-502692 A | 1/2017 |
| RU | 2600067 C2 | 10/2016 |
| WO | 93/24640 A2 | 12/1993 |
| WO | 94/16737 A1 | 8/1994 |
| WO | 98/17799 A1 | 4/1998 |
| WO | 99/43839 A1 | 9/1999 |
| WO | 03/00113 | 1/2003 |
| WO | 2005/000235 A2 | 1/2005 |
| WO | 2007/050095 A2 | 5/2007 |
| WO | 2007/087178 A2 | 8/2007 |
| WO | 2007/117371 A2 | 10/2007 |
| WO | 2009/124309 A2 | 10/2009 |
| WO | 2011/032179 A1 | 3/2011 |
| WO | 2011/097640 A1 | 8/2011 |
| WO | 2015/090584 A1 | 6/2015 |

OTHER PUBLICATIONS

English Translation of RU Office Action dated Nov. 23, 2020 for RU Application No. 2020122868.

Gerber et al., "Phosphatidylinositol glycan (PI-G) anchored membrane proteins. Amino acid requirements adjacent to the site of cleavage and PL-G attachment in the COOH-terminal signal peptide" The Journal of Biological Chemistry, vol. 267, No. 17, Issue of Jun. 15, 1992, pp. 12168-12173.

Hassan et al., "Mesothelin targeted cancer immunotherapy" European Journal of Cancer, vol. 44, 2008, pp. 46-53.

International Preliminary Report on Patentability and Written Opinion issued in PCT/US2018/065519, dated Jun. 25, 2020.

International Search Report and Written Opinion issued in PCT/US18/65519, dated May 14, 2019.

Kaneko et al., "A Binding Domain on Mesothelin for CA125/MUC16", J. Biol. Chem., vol. 284, No. 6, Feb. 6, 2009, pp. 3739-3749.

Kyte et al., "A Simple Method for Displaying the Hydropathic Character of a Protein" J. Mol. Biol., vol. 157, 1982, pp. 105-132.

Mayor et al., "Sorting GPI-Anchored Proteins" Nature reviews Molecular cell biology, vol. 5, Feb. 2004 pp. 110-120.

Muthumani et al., "Novel engineered HIV-1 East African Clade—A gp160 plasmid construct induces strong humoral and cell-mediated immune responses in vivo" Virology vol. 314, 2003, pp. 134-146.

Ordonez, "Application of Mesothelin Immunostaining in Tumor Diagnosis" Am. J. Surg. Pathol., vol. 27, No. 11, Nov. 2003, pp. 1418-1428.

Partial Supplementary European search report dated Aug. 19, 2021 for EP Application No. 18887384.

Saeki et al., "Prostate Stem Cell Antigen: A Jekyll and Hyde Molecule?" Molecular Pathways, Clinical Cancer Research, vol. 16 No. 14, Jul. 15, 2010, pp. 3533-3538.

Sathyanarayana et al., "Mesothelin, Stereocilin, and Otoancorin are predicted to have superhelical structures with ARM-type repeats" BMC Structural Biology, vol. 9, No. 1, Jan. 7, 2009 11 Pages.

Schneider et al., "Inactivation of the Human Immunodeficiency Virus Type 1 Inhibitory Elements Allows Rev-Independent Expression of Gag and Gag/Protease and Particle Formation" Journal of Virology, vol. 71, No. 7, Jul. 1997, pp. 4892-41903.

Seledtsov et al.; "Xenovaccinotherapy For Cancer Treatment"; Siberian Journal of Oncology; 2010; p. 48-57 (English Abstract).

Yan et al., "Preferred Sites of Glycosylphosphatidylinositol Modification in Folate Receptors and Constraints in the Primary Structure of the Hydrophobic Portion of the Signal" Biochemistry, vol. 34, 1995, pp. 14594-14600.

Yang et al., "Induction of Potent Th1-Type Immune Responses from a Novel DNA Vaccine or West Nile Virus New York Isolate (WNV-NY1999)" The Journal of infectious Diseases, vol. 184, 2001, pp. 309-816.

"Mesothelin isoform 1 preproprotein [*Homo sapiens*]"; NCBI Ref. Sequence NP_001170826.1; https://www.ncbi.nlm.nih.gov/protein/293651530?sat=46&satkey=70488340; accessed Nov. 19, 2021; 3 pages.

U.S. Appl. No. 16/219,287, filed Dec. 13, 2018.

CANCER VACCINES TARGETING MESOTHELIN AND USES THEREOF

CROSS-REFERENCE TO RELATED APPLICATIONS

This application is a divisional of U.S. patent application Ser. No. 16/219,287, filed Dec. 13, 2018, which claims priority to and the benefit of U.S. Provisional Patent Application No. 62/598,289, filed Dec. 13, 2017, the disclosure of each of which are incorporated herein by reference in their entirety.

SEQUENCE LISTING

This application contains a Sequence Listing which has been submitted electronically in ASCII format and is hereby incorporated by reference in its entirety. Said ASCII copy, created Sep. 7, 2021, is named 104409_000648_sequence_listing.txt and is 8,269 bytes in size.

TECHNICAL FIELD

The present invention relates to mesothelin antigens and nucleic acid molecules which encode the same. The present invention also relates to vaccines including the mesothelin antigens and/or nucleic acid molecules. The present invention further relates to methods of using the vaccines for inducing immune responses and preventing and/or treating subjects having mesothelin-expressing cancerous cells.

BACKGROUND

Cancer remains a major cause of death in the U.S. and worldwide. The cancer vaccine market is growing rapidly. Effective tumor vaccines may be useful to prevent tumor growth and/or may be useful as being a more effective, less toxic alternative to standard treatments for patients with advanced cancers. An antigen associated with cancer and, therefore, a target for anti-tumor vaccines is mesothelin.

Mesothelin is a 71 kD protein that is cleaved into two products: a 30 kD megakaryocyte potentiating factor and 41 kD GPI-anchored membrane-bound mature mesothelin. While the function of mesothelin is unknown, recent studies suggest that mesothelin may play a role in ovarian cancer metastasis by binding to MUC16, which is also highly expressed on the surface of ovarian cancer cells. Expression of mesothelin has been observed in 82-100% of serous ovarian carcinomas by IHC. Hassan, R. European journal of cancer 44, 46-53 (2008); Ordonez, N. G. The American journal of surgical pathology 27, 1418-1428 (2003). Because of its high expression in ovarian cancers as well as its association with tumor invasion, mesothelin is an attractive cancer therapeutic vaccine target.

Vaccines for the treatment and prevention of cancer are of great interest. Existing vaccines targeting tumor cell antigens are often limited by poor antigen expression in vivo. Accordingly, a need remains in the art for the development of safe and effective vaccines that are applicable to tumors expressing mesothelin, thereby providing treatment of and promoting survival of subjects afflicted with such cancers.

SUMMARY OF THE INVENTION

Provided herein are nucleic acid molecules comprising one or more nucleic acid sequences selected from the group consisting of: (a) a nucleic acid sequence that encodes amino acids 19-607 of SEQ ID NO: 2; (b) a nucleic acid sequence that encodes a fragment comprising at least 90% of an entire length of a protein comprising amino acids 19-607 of SEQ ID NO: 2; (c) a nucleic acid sequence that encodes a protein that is at least 96% identical to amino acids 19-607 of SEQ ID NO: 2; and (d) a nucleic acid sequence that encodes a fragment comprising at least 90% of an entire length of a protein that is at least 96% identical to amino acids 19-607 of SEQ ID NO: 2.

Also provided herein are nucleic acid molecules comprising one or more nucleic acid sequences selected from the group consisting of: nucleotides 55-1821 SEQ ID NO: 1; (b) a fragment comprising at least 90% an entire length of a nucleic acid molecule comprising nucleotides 55-1821 of SEQ ID NO: 1; (c) a fragment that is at least 96% identical to nucleotides 55-1821 of SEQ ID NO: 1; and (d) a fragment comprising at least 90% of an entire length of a nucleic acid sequence that is at least 96% identical to nucleotides 55-1821 of SEQ ID NO: 1.

Provided herein are nucleic acid molecules comprising one or more nucleic acid sequences selected from the group consisting of: (a) a nucleic acid sequence that encodes SEQ ID NO: 2; (b) a nucleic acid sequence that encodes a fragment comprising at least 90% of an entire length of SEQ ID NO: 2; (c) a nucleic acid sequence that encodes a protein that is at least 96% identical to SEQ ID NO: 2; and (d) a nucleic acid sequence that encodes a fragment comprising at least 90% of an entire length of a protein that is at least 96% identical to SEQ ID NO: 2.

Also provided herein are nucleic acid molecules comprising one or more nucleic acid sequences selected from the group consisting of: (a) SEQ ID NO: 1; (b) a fragment comprising at least 90% of an entire length of SEQ ID NO: 1; (c) a fragment that is at least 96% identical to SEQ ID NO: 1; and (d) a fragment comprising at least 90% of an entire length of a nucleic acid sequence that is at least 96% identical to SEQ ID NO: 1. In some embodiments, the nucleic acid molecule comprises the nucleic acid sequence set forth in SEQ ID NO: 1.

The nucleic acid molecules described herein may be incorporated into a vector, such as a plasmid or viral vector. In some embodiments, the vector comprises nucleic acid molecules comprising one or more nucleic acid sequences selected from the group consisting of: (a) a nucleic acid sequence that encodes amino acids 19-607 of SEQ ID NO: 2; (b) a nucleic acid sequence that encodes a fragment comprising at least 90% of an entire length of a protein comprising amino acids 19-607 of SEQ ID NO: 2; (c) a nucleic acid sequence that encodes a protein that is at least 96% identical to amino acids 19-607 of SEQ ID NO: 2; and (d) a nucleic acid sequence that encodes a fragment comprising at least 90% of an entire length of a protein that is at least 96% identical to amino acids 19-607 of SEQ ID NO: 2. In further embodiments, the vector comprises nucleic acid molecules comprising one or more nucleic acid sequences selected from the group consisting of: nucleotides 55-1821 SEQ ID NO: 1; (b) a fragment comprising at least 90% an entire length of a nucleic acid molecule comprising nucleotides 55-1821 of SEQ ID NO: 1; (c) a fragment that is at least 96% identical to nucleotides 55-1821 of SEQ ID NO: 1; and (d) a fragment comprising at least 90% of an entire length of a nucleic acid sequence that is at least 96% identical to nucleotides 55-1821 of SEQ ID NO: 1. In still further embodiments, the vector comprises nucleic acid molecules comprising one or more nucleic acid sequences selected from the group consisting of: (a) a nucleic acid sequence that encodes SEQ ID NO: 2; (b) a nucleic acid sequence that encodes a fragment comprising at least 90% of an entire length of SEQ ID NO: 2; (c) a nucleic acid sequence that encodes a protein that is at least 96% identical to SEQ ID NO: 2; and (d) a nucleic acid sequence that encodes a fragment comprising at least 90% of an entire length of a protein that is at least 96% identical to SEQ ID NO: 2. In further embodiments, the vector comprises nucleic acid molecules comprising one or more nucleic acid sequences selected from the group consisting of: (a) SEQ ID NO: 1; (b) a fragment comprising at least 90% of an entire length of SEQ ID NO: 1; (c) a fragment that is at least 96% identical to SEQ ID NO: 1; and (d) a fragment comprising at least 90% of an entire length of a nucleic acid sequence that is at least 96% identical to SEQ ID NO: 1. In still further embodiments, the vector comprises the nucleic acid sequence set forth in SEQ ID NO: 1.

In some embodiments, the nucleic acids described herein are operably linked to a regulatory element. In some embodiments the regulatory element is a promoter and/or a poly-adenylation signal. In further embodiments, the promoter is a human cytomegalovirus immediate-early promoter (hCMV promoter). In still further embodiments, the poly-adenylation signal is a bovine growth hormone poly-adenylation signal (bGH polyA).

Also provided herein are compositions comprising one or more nucleic acid molecules as described herein. In some embodiments, the compositions comprise a pharmaceutically acceptable carrier.

Further provided are mesothelin antigenic proteins comprising the amino acid sequence selected from the group consisting of: (a) amino acids 19-607 of SEQ ID NO: 2; (b) a fragment comprising at least 90% of an entire length of a protein comprising amino acids 19-607 of SEQ ID NO: 2; (c) an amino acid sequence that is at least 95% identical to amino acids 19-607 of SEQ ID NO: 2; and (d) a fragment comprising at least 90% of an entire length of an amino acid sequence that is at least 95% identical to amino acids 19-607 of SEQ ID NO: 2.

Further provided are mesothelin antigenic proteins comprising the amino acid sequence selected from the group consisting of: (a) SEQ ID NO: 2; (b) a fragment comprising at least 90% of an entire length of SEQ ID NO: 2; (c) an amino acid sequence that is at least 96% identical to SEQ ID NO: 2; and (c) a fragment comprising at least 90% of an entire length of an amino acid sequence that is at least 96% identical to SEQ ID NO: 2. In some embodiments, the protein comprises the amino acid sequence set forth in SEQ ID NO: 2.

Vaccines comprising a mesothelin antigen wherein the antigen comprises the amino acid sequence set forth in SEQ ID NO: 2 also are provided. In some embodiments, the antigen is encoded by SEQ ID NO: 1.

Further provided are vaccines comprising a nucleic acid molecule wherein the nucleic acid molecule comprises a nucleic acid sequence having at least about 96% identity over an entire length of the nucleic acid sequence set forth in SEQ ID NO: 1. Further disclosed herein are vaccines comprising a nucleic acid molecule wherein the nucleic acid molecule encodes a mesothelin antigen comprising an amino acid sequence having at least about 96% identity over an entire length of the amino acid sequence set forth in SEQ ID NO: 2. In some embodiments, the nucleic acid molecule may comprise an expression vector. The vaccines may further comprise a pharmaceutically acceptable excipient. In some embodiments, the vaccines may further comprise an adjuvant. In certain embodiments, the adjuvant is IL-12, IL-15, IL-28, or RANTES.

Also provided herein are vaccines comprising a mesothelin antigen, wherein the antigen comprises an amino acid sequence having at least about 90% identity over an entire length of the amino acid sequence set forth in SEQ ID NO: 2.

Further provided are methods of treating a subject with a mesothelin-expressing cancerous cell comprising administering a therapeutically effective amount of a vaccine described herein. In some embodiments, the administration includes an electroporation step. In other embodiments, the administration occurs at one or more sites on the subject.

Methods of vaccinating a subject against a mesothelin-expressing cancerous cell comprising administering an amount of a vaccine described herein effective to induce a humoral immune response also are provided. In some embodiments, the administration includes an electroporation step. In other embodiments, the administration occurs at one or more sites on the subject.

Also provided herein are nucleic acid molecules comprising one or more nucleic acid sequences selected from the group consisting of: (a) a nucleic acid sequence that encodes SEQ ID NO: 2; (b) a nucleic acid sequence that encodes a fragment comprising at least 90% of an entire length of SEQ ID NO: 2; (c) a nucleic acid sequence that encodes a protein that is at least 96% identical to SEQ ID NO: 2; and (d) a nucleic acid sequence that encodes a fragment comprising at least 90% of an entire length of a protein that is at least 96% identical to SEQ ID NO: 2 for use as a medicament. In some embodiments, the nucleic acid molecules described herein are for use as a medicament in the treatment of cancer. In some embodiments, the nucleic acid molecules described herein are for use in the preparation of a medicament. In some embodiments, the nucleic acid molecules described herein are for use in the preparation of a medicament for the treatment of cancer.

Also provided herein are nucleic acid molecules comprising one or more nucleic acid sequences selected from the group consisting of: (a) SEQ ID NO: 1; (b) a fragment comprising at least 90% of an entire length of SEQ ID NO: 1; (c) a fragment that is at least 96% identical to SEQ ID NO: 1; and (d) a fragment comprising at least 90% of an entire length of a nucleic acid sequence that is at least 96% identical to SEQ ID NO: 1. In some embodiments, the nucleic acid molecule comprises the nucleic acid sequence set forth in SEQ ID NO: 1 for use as a medicament. In some embodiments, the nucleic acid molecules described herein are for use as a medicament in the treatment of cancer. In some embodiments, the nucleic acid molecules described herein are for use in the preparation of a medicament. In some embodiments, the nucleic acid molecules described herein are for use in the preparation of a medicament for the treatment of cancer.

BRIEF DESCRIPTION OF THE DRAWINGS

FIG. 9A shows synthetic consensus mesothelin induced frequencies of antigen specific CD4+ T cell responses. FIG. 9B shows synthetic consensus mesothelin induced frequencies of antigen specific CD8+ T cell responses. FIG. 9C shows the cytokine profile of synthetic consensus mesothelin specific CD4+ T cells. FIG. 9D shows the cytokine profile of synthetic consensus mesothelin specific CD8+ T cells.

FIG. 10A shows the frequency of antigen specific CD4+CD107a+ T cells. FIG. 10B shows the frequency of antigen specific CD8+CD107a+ T cells. FIG. 10C shows the cytokine profile of synthetic consensus mesothelin specific CD4+CD107a+ T cells. FIG. 10D shows the cytokine profile of synthetic consensus mesothelin specific CD8+CD107a+ T cells.

FIG. 11A shows mesothelin alone, FIG. 11B shows mesothelin with a low dose of IL-12 (0.04 mg), and FIG. 11C shows mesothelin with a high dose of IL-12 (0.2 mg).

FIG. 12A shows mesothelin alone, FIG. 12B shows mesothelin with a low dose of IL-12 (0.04 mg), and FIG. 12C shows mesothelin with a high dose of IL-12 (0.2 mg).

DETAILED DESCRIPTION

Figure 1:
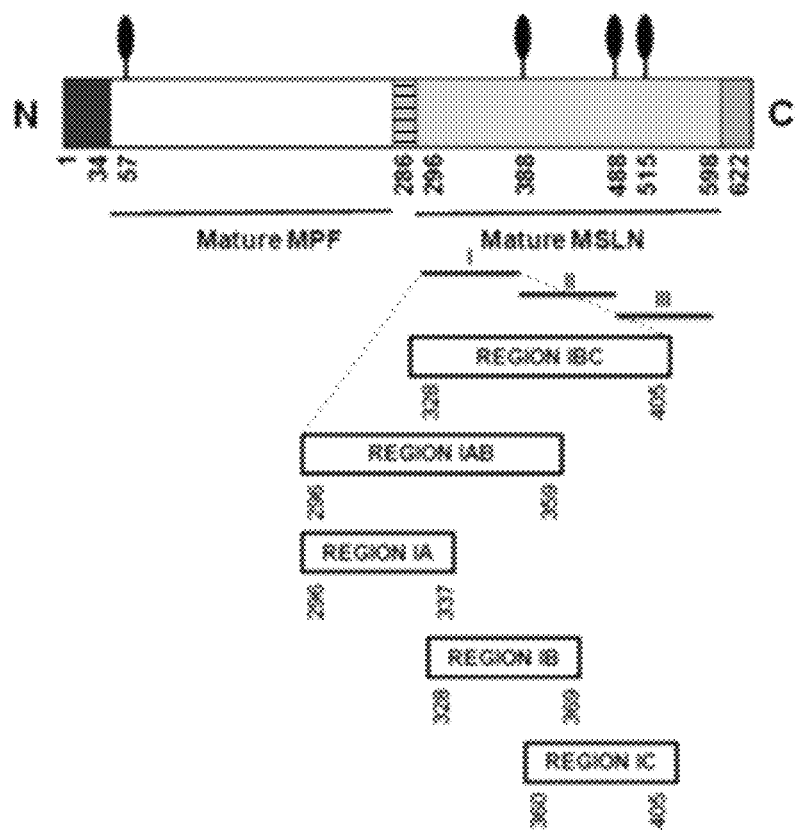
FIG. 1 illustrates the generation of mesothelin mutants.

The present invention relates to vaccines comprising a mesothelin antigen. Mesothelin is expressed in many tumors. Accordingly, the vaccines provide treatment for a cancer or tumor expressing mesothelin. The vaccine of the invention can provide any combination of particular cancer antigens for the particular prevention or treatment of the cancer of a subject that is in need of treatment.

One manner for designing the nucleic acid and its' encoded amino acid sequence of the recombinant cancer antigen is by introducing mutations that change particular amino acids in the overall amino acid sequence of the native cancer antigen. The introduction of mutations does not alter the cancer antigen so much that it cannot be universally applied across a mammalian subject, and preferably a human or dog subject, but changes it enough that the resulting amino acid sequence breaks tolerance or is considered a foreign antigen in order to generate an immune response. Another manner may be creating a consensus recombinant cancer antigen that has at least 85% and up to 99% amino acid sequence identity to its' corresponding native cancer antigen; preferably at least 90% and up to 98% sequence identity; more preferably at least 93% and up to 98% sequence identity; or even more preferably at least 95% and up to 98% sequence identity. In some instances the recombinant cancer antigen is 95%, 96%, 97%, 98%, or 99% amino acid sequence identity to its' corresponding native cancer antigen. The native cancer antigen is the antigen normally associated with the particular cancer or cancer tumor. Depending upon the cancer antigen, the consensus sequence of the cancer antigen can be across mammalian species or within subtypes of a species or across viral strains or serotypes. Some cancer antigens do not vary greatly from the wild type amino acid sequence of the cancer antigen. Some cancer antigens have nucleic acid/amino acid sequences that are so divergent across species, that a consensus sequence cannot be generated. In these instances, a recombinant cancer antigen that will break tolerance and generate an immune response is generated that has at least 85% and up to 99% amino acid sequence identity to its' corresponding native cancer antigen; preferably at least 90% and up to 98% sequence identity; more preferably at least 93% and up to 98% sequence identity; or even more preferably at least 95% and up to 98% sequence identity. In some instances the recombinant cancer antigen is 95%, 96%, 97%, 98%, or 99% amino acid sequence identity to its' corresponding native cancer antigen. The aforementioned approaches can be combined so that the final recombinant cancer antigen has a percent similarity to native cancer antigen amino acid sequence as discussed, above.

The mesothelin antigen can be a consensus mesothelin antigen derived, in part, from the sequences of mesothelin from different species or from different isoforms within a species, and thus, the consensus mesothelin antigen is non-native. Modifications may include mutations of to the MUC16 binding domain and/or to the GPI-anchoring signal, and the addition of upstream Kozak and IgE leader sequences to the N-terminus of the mesothelin antigen.

The synthetic mesothelin can induce antigen-specific T cell and/or high titer antibody responses, thereby inducing or eliciting an immune response that is directed to or reactive against the cancer or tumor expressing the antigen. In some embodiments, the induced or elicited immune response can be a cellular, humoral, or both cellular and humoral immune responses. In some embodiments, the induced or elicited cellular immune response can include induction or secretion of interferon-gamma (IFN-γ) and/or tumor necrosis factor alpha (TNF-α). In other embodiments, the induced or elicited immune response can reduce or inhibit one or more immune suppression factors that promote growth of the tumor or cancer expressing the antigen, for example, but not limited to, factors that down regulate MHC presentation, factors that up regulate antigen-specific regulatory T cells (Tregs), PD-L1, FasL, cytokines such as IL-10 and TFG-β, tumor associated macrophages, tumor associated fibroblasts, soluble factors produced by immune suppressor cells, CTLA-4, PD-1, MDSCs, MCP-1, and an immune checkpoint molecule.

The vaccine may be combined further with antibodies to checkpoint inhibitors such as PD-1 and PDL-1 to increase the stimulation of both the cellular and humoral immune responses. Using anti-PD-1 or anti-PDL-1 antibodies prevents PD-1 or PDL-1 from suppressing T-cell and/or B-cell responses. Overall, by designing the cancer antigens to be recognized by the immune system helps to overcome other forms of immune suppression by tumor cells, and these vaccines can be used in combination with suppression or inhibition therapies (such as anti-PD-1 and anti-PDL-1 antibody therapies) to further increase T-cell and/or B-cell responses.

Definitions

Unless otherwise defined, all technical and scientific terms used herein have the same meaning as commonly understood by one of ordinary skill in the art. In case of conflict, the present document, including definitions, will control. Preferred methods and materials are described below, although methods and materials similar or equivalent to those described herein can be used in practice or testing of the present invention. All publications, patent applications, patents and other references mentioned herein are incorporated by reference in their entirety. The materials, methods, and examples disclosed herein are illustrative only and not intended to be limiting. The terminology used herein is for the purpose of describing particular embodiments only and is not intended to be limiting.

The terms "comprise(s)," "include(s)," "having," "has," "can," "contain(s)," and variants thereof, as used herein, are intended to be open-ended transitional phrases, terms, or words that do not preclude the possibility of additional acts or structures. The singular forms "a," "and" and "the" include plural references unless the context clearly dictates otherwise. The present disclosure also contemplates other embodiments "comprising," "consisting of" and "consisting essentially of," the embodiments or elements presented herein, whether explicitly set forth or not.

For recitation of numeric ranges herein, each intervening value having the same degree of precision as the recited range minimum and maximum is explicitly contemplated. For example, for the range of 6-9, the numbers 7 and 8 are contemplated in addition to 6 and 9, and for the range 6.0-7.0, the numbers 6.0, 6.1, 6.2, 6.3, 6.4, 6.5, 6.6, 6.7, 6.8, 6.9, and 7.0 are explicitly contemplated.

"Adjuvant" as used herein means any molecule added to the vaccines described herein to enhance the immunogenicity of the mesothelin antigens and/or the nucleic acid molecules encoding the antigens as described herein.

"Antibody" as used herein means an antibody of classes IgG, IgM, IgA, IgD, or IgE, or fragments, or derivatives thereof, including Fab, F(ab')2, Fd, and single chain antibodies, diabodies, bispecific antibodies, bifunctional antibodies, and derivatives thereof. The antibody can be an antibody isolated from the serum sample of a mammal, a polyclonal antibody, an affinity purified antibody, or any mixture thereof which exhibits sufficient binding specificity to a desired epitope or a sequence derived therefrom.

"Mesothelin antigen" refers to: proteins having mutated mesothelin amino acid sequences including amino acids 19-607 of SEQ ID NO: 2; SEQ ID NO: 2; fragments thereof of lengths set forth herein, variants, i.e. proteins with sequences having identity to SEQ ID NO: 2 as set forth herein, fragments of variants having lengths set forth herein, SEQ ID NO: 2; fragments thereof of lengths set forth herein, variants, i.e. proteins with sequences having identity to SEQ ID NO: 2 as set forth herein, fragments of variants having lengths set forth herein, and combinations thereof. Antigens may optionally include signal peptides such as those from other proteins.

"Coding sequence" or "encoding nucleic acid" as used herein means the nucleic acids (RNA or DNA molecule) that comprise a nucleotide sequence which encodes a protein. The coding sequence can further include initiation and termination signals operably linked to regulatory elements including a promoter and polyadenylation signal capable of directing expression in the cells of a subject or mammal to which the nucleic acid is administered.

"Complement" or "complementary" as used herein means a nucleic acid can mean Watson-Crick (e.g., A-T/U and C-G) or Hoogsteen base pairing between nucleotides or nucleotide analogs of nucleic acid molecules.

"Consensus" or "consensus sequence" as used herein means a polypeptide sequence based on analysis of an alignment of multiple sequences for the same gene from different organisms. Nucleic acid sequences that encode a consensus polypeptide sequence can be prepared. Vaccines comprising proteins that comprise consensus sequences and/or nucleic acid molecules that encode such proteins can be used to induce broad immunity against an antigen.

"Constant current" as used herein describes a current that is received or experienced by a tissue, or cells defining said tissue, over the duration of an electrical pulse delivered to same tissue. The electrical pulse is delivered from the electroporation devices described herein. This current remains at a constant amperage in said tissue over the life of an electrical pulse because the electroporation device provided herein has a feedback element, preferably having instantaneous feedback. The feedback element can measure the resistance of the tissue (or cells) throughout the duration of the pulse and cause the electroporation device to alter its electrical energy output (e.g., increase voltage) so current in same tissue remains constant throughout the electrical pulse (on the order of microseconds), and from pulse to pulse. In some embodiments, the feedback element comprises a controller.

"Current feedback" or "feedback" as used herein may be used interchangeably and may mean the active response of the provided electroporation devices, which comprises measuring the current in tissue between electrodes and altering the energy output delivered by the EP device accordingly in order to maintain the current at a constant level. This constant level is preset by a user prior to initiation of a pulse sequence or electrical treatment. The feedback may be accomplished by the electroporation component, e.g., controller, of the electroporation device, as the electrical circuit therein is able to continuously monitor the current in tissue between electrodes and compare that monitored current (or current within tissue) to a preset current and continuously make energy-output adjustments to maintain the monitored current at preset levels. The feedback loop may be instantaneous as it is an analog closed-loop feedback.

"Decentralized current" as used herein may mean the pattern of electrical currents delivered from the various needle electrode arrays of the electroporation devices described herein, wherein the patterns minimize, or preferably eliminate, the occurrence of electroporation related heat stress on any area of tissue being electroporated.

"Electroporation," "electro-permeabilization," or "electro-kinetic enhancement" ("EP") as used interchangeably herein means the use of a transmembrane electric field pulse to induce microscopic pathways (pores) in a bio-membrane; their presence allows biomolecules such as plasmids, oligonucleotides, siRNA, drugs, ions, and water to pass from one side of the cellular membrane to the other.

"Fragment" as used herein with respect to nucleic acid sequences means a nucleic acid sequence or a portion thereof, that encodes a polypeptide capable of eliciting an immune response in a mammal that cross reacts with an antigen disclosed herein. The fragments can be DNA fragments selected from at least one of the various nucleotide sequences that encode protein fragments set forth below. Fragments can comprise at least 10%, at least 20%, at least 30%, at least 40%, at least 50%, at least 60%, at least 70%, at least 80%, at least 90%, or at least 95% of an entire length of one or more of the nucleic acid sequences described herein, excluding any heterologous signal peptide added. In some embodiments, fragments can comprise at least 90%, at least 91%, at least 92%, at least 93%, at least 94%, at least 95%, at least 96%, at least 97%, at least 98%, or at least 99% of an entire length of one or more of the nucleic acid sequences set forth below, excluding any heterologous signal peptide added.

In some embodiments, the fragments may be at least 10%, at least 20%, at least 30%, at least 40%, at least 50%, at least 60%, at least 70%, at least 80%, at least 90%, or at least 95% identical to one or more of nucleic acid sequences described herein, excluding any heterologous signal peptide. In some embodiments, the fragments may be at least 96%, at least 97%, at least 98%, or at least 99% identical to one or more of the nucleic acid sequences set forth below, excluding any heterologous signal peptide added.

In further embodiments, the fragments may additionally optionally comprise sequence encoding a heterologous signal peptide which is not included when calculating percent identity. Fragments may also comprise coding sequences for a signal peptide such as an immunoglobulin signal peptide, for example an IgE or IgG signal peptide. The coding sequence encoding an N terminal methionine and/or signal peptide may be linked to a fragment of coding sequence.

In some embodiments, fragments can comprise at least 1500 nucleotides or more, 1510 nucleotides or more, 1520 nucleotides or more, 1530 nucleotides or more, 1540 nucleotides or more, 1550 nucleotides or more, 1560 nucleotides or more, 1570 nucleotides or more, 1580 nucleotides or more, 1590 nucleotides or more, 1600 nucleotides or more, 1610 nucleotides or more, 1620 nucleotides or more, or 1630 nucleotides or more, 1640 nucleotides or more, 1650 nucleotides or more, 1660 nucleotides or more, 1670 nucleotides or more, 1680 nucleotides or more, 1690 nucleotides or more, 1700 nucleotides or more, 1710 nucleotides or more, 1720 nucleotides or more, 1730 nucleotides or more, 1740 nucleotides or more, 1750 nucleotides or more, 1760 nucleotides or more, 1770 nucleotides or more, 1780 nucleotides or more, 1790 nucleotides or more, 1800 nucleotides or more, 1810 nucleotides or more, or 1820 nucleotides or more of at least one of the nucleic acid sequences set forth below.

"Fragment" or "immunogenic fragment" with respect to polypeptide sequences means a polypeptide capable of eliciting an immune response in a mammal that cross reacts with an antigen disclosed herein. The fragments can be polypeptide fragments selected from at least one of the various amino acid sequences described herein. Fragments of consensus proteins can comprise at least 10%, at least 20%, at least 30%, at least 40%, at least 50%, at least 60%, at least 70%, at least 80%, at least 90% or at least 95% of an entire length of a consensus protein, excluding any heterologous signal peptide added. In some embodiments, the fragment may comprise at least 90%, at least 91%, at least 92%, at least 93%, at least 94%, at least 95%, at least 96%, at least 97%, at least 98%, or at least 99% of the length of one or more of the amino sequences set forth below, excluding any heterologous signal peptide added.

In some embodiments, the fragments may be at least 10%, at least 20%, at least 30%, at least 40%, at least 50%, at least 60%, at least 70%, at least 80%, at least 90%, or at least 95% identical to one or more of amino acid sequences described herein, excluding any heterologous signal peptide. In some embodiments, the fragments may be at least 96%, at least 97%, at least 98%, or at least 99% identical to one or more of the amino acid sequences set forth below, excluding any heterologous signal peptide added In further embodiments, the fragments may additionally optionally comprise sequence encoding a heterologous signal peptide which is not included when calculating percent identity. Fragments may further comprise a signal peptide such as an immunoglobulin signal peptide, for example an IgE or IgG signal peptide.

In some embodiments, fragments of consensus proteins can comprise at least 546 amino acids or more, 547 amino acids or more, 548 amino acids or more, 549 amino acids or more, 550 amino acids or more, 551 amino acids or more, 552 amino acids or more, 553 amino acids or more, 554 amino acids or more, 555 amino acids or more, 556 amino acids or more, 557 amino acids or more, 558 amino acids or more, 559 amino acids or more, 560 amino acids or more, 561 amino acids or more, 562 amino acids or more, 563 amino acids or more, 564 amino acids or more, 565 amino acids or more, 566 amino acids or more, 567 amino acids or more, 568 amino acids or more, 569 amino acids or more, 570 amino acids or more, 571 amino acids or more, 572 amino acids or more, 573 amino acids or more, 574 amino acids or more, 575 amino acids or more, 576 amino acids or more, 577 amino acids or more, 578 amino acids or more, 579 amino acids or more, 580 amino acids or more, 581 amino acids or more, 582 amino acids or more, 583 amino acids or more, 584 amino acids or more, 585 amino acids or more, 586 amino acids or more, 587 amino acids or more, 588 amino acids or more, 589 amino acids or more, 590 amino acids or more, 591 amino acids or more, 592 amino acids or more, 593 amino acids or more, 594 amino acids or more, 595 amino acids or more, 596 amino acids or more, 597 amino acids or more, 598 amino acids or more, 599 amino acids or more, 600 amino acids or more, 601 amino acids or more, 602 amino acids or more, 603 amino acids or more, 604 amino acids or more, 605 amino acids or more, 606 amino acids or more, 607 of a protein sequence disclosed herein.

As used herein, the term "genetic construct" refers to the DNA or RNA molecules that comprise a nucleotide sequence that encodes a protein. The coding sequence includes initiation and termination signals operably linked to regulatory elements including a promoter and polyadenylation signal capable of directing expression in the cells of the subject to whom the nucleic acid molecule is administered. As used herein, the term "expressible form" refers to a gene construct that contains the necessary regulatory elements operably linked to a coding sequence that encodes a protein such that, when present in a cell of a subject, the coding sequence will be expressed.

The term "homology," as used herein, refers to a degree of complementarity. There can be partial homology or complete homology (i.e., identity). A partially complementary sequence that at least partially inhibits a completely complementary sequence from hybridizing to a target nucleic acid is referred to using the functional term "substantially homologous." When used in reference to a double-stranded nucleic acid sequence such as a cDNA or genomic clone, the term "substantially homologous," as used herein, refers to a probe that can hybridize to a strand of the double-stranded nucleic acid sequence under conditions of low stringency. When used in reference to a single-stranded nucleic acid sequence, the term "substantially homologous," as used herein, refers to a probe that can hybridize to (i.e., is the complement of) the single-stranded nucleic acid template sequence under conditions of low stringency.

"Identical" or "identity" as used herein in the context of two or more nucleic acids or polypeptide sequences means that the sequences have a specified percentage of residues that are the same over a specified region. The percentage can be calculated by optimally aligning the two sequences, comparing the two sequences over the specified region, determining the number of positions at which the identical residue occurs in both sequences to yield the number of matched positions, dividing the number of matched positions by the total number of positions in the specified region, and multiplying the result by 100 to yield the percentage of sequence identity. In cases where the two sequences are of different lengths or the alignment produces one or more staggered ends and the specified region of comparison includes only a single sequence, the residues of single sequence are included in the denominator but not the numerator of the calculation. When comparing DNA and RNA, thymine (T) and uracil (U) can be considered equivalent. Identity can be performed manually or by using a computer sequence algorithm such as BLAST or BLAST 2.0.

"Impedance" as used herein may be used when discussing the feedback mechanism and can be converted to a current value according to Ohm's law, thus enabling comparisons with the preset current.

"Immune response" as used herein means the activation of a host's immune system, e.g., that of a mammal, in response to the introduction of antigen. The immune response can be in the form of a cellular or humoral response, or both.

"Nucleic acid" or "oligonucleotide" or "polynucleotide" as used herein means at least two nucleotides covalently linked together. The depiction of a single strand also defines the sequence of the complementary strand. Thus, a nucleic acid also encompasses the complementary strand of a depicted single strand. Many variants of a nucleic acid can be used for the same purpose as a given nucleic acid. Thus, a nucleic acid also encompasses substantially identical nucleic acids and complements thereof. A single strand provides a probe that can hybridize to a target sequence under stringent hybridization conditions. Thus, a nucleic acid also encompasses a probe that hybridizes under stringent hybridization conditions.

Nucleic acids can be single stranded or double stranded, or can contain portions of both double stranded and single stranded sequence. The nucleic acid can be DNA, both genomic and cDNA, RNA, or a hybrid, where the nucleic acid can contain combinations of deoxyribo- and ribo-nucleotides, and combinations of bases including uracil, adenine, thymine, cytosine, guanine, inosine, xanthine hypoxanthine, isocytosine and isoguanine. Nucleic acids can be obtained by chemical synthesis methods or by recombinant methods.

"Operably linked" as used herein means that expression of a gene is under the control of a promoter with which it is spatially connected. A promoter can be positioned 5' (upstream) or 3' (downstream) of a gene under its control. The distance between the promoter and a gene can be approximately the same as the distance between that promoter and the gene it controls in the gene from which the promoter is derived. As is known in the art, variation in this distance can be accommodated without loss of promoter function.

A "peptide," "protein," or "polypeptide" as used herein can mean a linked sequence of amino acids and can be natural, synthetic, or a modification or combination of natural and synthetic.

"Promoter" as used herein means a synthetic or naturally derived molecule which is capable of conferring, activating, or enhancing expression of a nucleic acid in a cell. A promoter can comprise one or more specific transcriptional regulatory sequences to further enhance expression and/or to alter the spatial expression and/or temporal expression of a nucleic acid in a cell. A promoter can also comprise distal enhancer or repressor elements, which can be located as much as several thousand base pairs from the start site of transcription. A promoter can be derived from sources including viral, bacterial, fungal, plant, insect, and animal. A promoter can regulate the expression of a gene component constitutively or differentially with respect to cell, tissue, or organ in which expression occurs, or with respect to the developmental stage at which expression occurs, or in response to external stimuli such as physiological stresses, pathogens, metal ions, or inducing agents. Representative examples of promoters include the bacteriophage T7 promoter, bacteriophage T3 promoter, SP6 promoter, lac operator-promoter, tac promoter, SV40 late promoter, SV40 early promoter, RSV-LTR promoter, CMV IE promoter, SV40 early promoter or SV40 late promoter, CMV IE promoter and human cytomegalovirus immediate-early promoter (hCMV). In certain embodiments, the promoter is a hCMV promoter.

"Signal peptide" and "leader sequence" are used interchangeably herein and refer to an amino acid sequence that can be linked at the amino terminus of a protein set forth herein. Signal peptides/leader sequences typically direct localization of a protein. Signal peptides/leader sequences used herein preferably facilitate secretion of the protein from the cell in which it is produced. Signal peptides/leader sequences are often cleaved from the remainder of the protein, often referred to as the mature protein, upon secretion from the cell. Signal peptides/leader sequences are linked at the amino terminus (i.e., N terminus) of the protein.

"Stringent hybridization conditions" as used herein means conditions under which a first nucleic acid sequence (e.g., probe) will hybridize to a second nucleic acid sequence (e.g., target), such as in a complex mixture of nucleic acids. Stringent conditions are sequence-dependent and will be different in different circumstances. Stringent conditions can be selected to be about 5-10° C. lower than the thermal melting point (Tm) for the specific sequence at a defined ionic strength pH. The Tm can be the temperature (under defined ionic strength, pH, and nucleic concentration) at which 50% of the probes complementary to the target hybridize to the target sequence at equilibrium (as the target sequences are present in excess, at Tm, 50% of the probes are occupied at equilibrium). Stringent conditions can be those in which the salt concentration is less than about 1.0 M sodium ion, such as about 0.01-1.0 M sodium ion concentration (or other salts) at pH 7.0 to 8.3 and the temperature is at least about 30° C. for short probes (e.g., about 10-50 nucleotides) and at least about 60° C. for long probes (e.g., greater than about 50 nucleotides). Stringent conditions can also be achieved with the addition of destabilizing agents such as formamide. For selective or specific hybridization, a positive signal can be at least 2 to 10 times background hybridization. Exemplary stringent hybridization conditions include the following: 50% formamide, 5×SSC, and 1% SDS, incubating at 42° C., or, 5×SSC, 1% SDS, incubating at 65° C., with wash in 0.2×SSC, and 0.1% SDS at 65° C.

"Subject" as used herein can mean a mammal that wants to or is in need of being immunized with the herein described vaccines. The mammal can be a human, a non-human primate such as a chimpanzee, a dog, a cat, a horse, a cow, a mouse, or a rat.

"Substantially complementary" as used herein means that a first sequence is at least 60%, 65%, 70%, 75%, 80%, 81%, 82%, 83%, 84%, 85%, 86%, 87%, 88%, 89%, 90%, 91%, 92%, 93%, 94%, 95%, 96%, 97%, 98% or 99% identical to the complement of a second sequence over a region of 8, 9, 10, 11, 12, 13, 14, 15, 16, 17, 18, 19, 20, 21, 22, 23, 24, 25, 30, 35, 40, 45, 50, 55, 60, 65, 70, 75, 80, 85, 90, 95, 100, 180, 270, 360, 450, 540, or more nucleotides or amino acids, or that the two sequences hybridize under stringent hybridization conditions.

"Substantially identical" as used herein means that a first and second sequence are at least 60%, 65%, 70%, 75%, 80%, 81%, 82%, 83%, 84%, 85%, 86%, 87%, 88%, 89%, 90%, 91%, 92%, 93%, 94%, 95%, 96%, 97%, 98% or 99% identical over a region of 8, 9, 10, 11, 12, 13, 14, 15, 16, 17, 18, 19, 20, 21, 22, 23, 24, 25, 30, 35, 40, 45, 50, 55, 60, 65, 70, 75, 80, 85, 90, 95, 100, 180, 270, 360, 450, 540 or more nucleotides or amino acids, or with respect to nucleic acids, if the first sequence is substantially complementary to the complement of the second sequence.

"Treat," "treatment," or "treating" as used herein can mean protecting an animal from a disease through means of preventing, suppressing, repressing, or completely eliminating the disease. Preventing the disease involves administering a vaccine of the present invention to an animal prior to onset of the disease. Suppressing the disease involves administering a vaccine of the present invention to an animal after induction of the disease but before its clinical appearance. Repressing the disease involves administering a vaccine of the present invention to an animal after clinical appearance of the disease.

"Variant" as used herein with respect to a nucleic acid means (i) a portion or fragment of a referenced nucleotide sequence; (ii) the complement of a referenced nucleotide sequence or portion thereof; (iii) a nucleic acid that is substantially identical to a referenced nucleic acid or the complement thereof; or (iv) a nucleic acid that hybridizes under stringent conditions to the referenced nucleic acid, complement thereof, or a sequence substantially identical thereto.

"Variant" as used herein with respect to a peptide or polypeptide means a peptide or polypeptide that differs in amino acid sequence by the insertion, deletion, or conservative substitution of amino acids, but retains at least one biological activity. Variant can also mean a protein with an amino acid sequence that is substantially identical to a referenced protein with an amino acid sequence that retains at least one biological activity. A conservative substitution of an amino acid, i.e., replacing an amino acid with a different amino acid of similar properties (e.g., hydrophilicity, degree and distribution of charged regions) is recognized in the art as typically involving a minor change. These minor changes can be identified, in part, by considering the hydropathic index of amino acids, as understood in the art. Kyte et al., J. Mol. Biol. 157:105-132 (1982). The hydropathic index of an amino acid is based on a consideration of its hydrophobicity and charge. It is known in the art that amino acids of similar hydropathic indexes can be substituted and still retain protein function. In one aspect, amino acids having hydropathic indexes of ±2 are substituted. The hydrophilicity of amino acids can also be used to reveal substitutions that would result in proteins retaining biological function. A consideration of the hydrophilicity of amino acids in the context of a peptide permits calculation of the greatest local average hydrophilicity of that peptide, a useful measure that has been reported to correlate well with antigenicity and immunogenicity. U.S. Pat. No. 4,554,101, incorporated fully herein by reference. Substitution of amino acids having similar hydrophilicity values can result in peptides retaining biological activity, for example immunogenicity, as is understood in the art. Substitutions can be performed with amino acids having hydrophilicity values within ±2 of each other. Both the hydrophobicity index and the hydrophilicity value of amino acids are influenced by the particular side chain of that amino acid. Consistent with that observation, amino acid substitutions that are compatible with biological function are understood to depend on the relative similarity of the amino acids, and particularly the side chains of those amino acids, as revealed by the hydrophobicity, hydrophilicity, charge, size, and other properties.

A variant may be a nucleic acid sequence that is substantially identical over the full length of the full gene sequence or a fragment thereof. The nucleic acid sequence may be 80%, 81%, 82%, 83%, 84%, 85%, 86%, 87%, 88%, 89%, 90%, 91%, 92%, 93%, 94%, 95%, 96%, 97%, 98%, 99%, or 100% identical over the full length of the gene sequence or a fragment thereof. A variant may be an amino acid sequence that is substantially identical over the full length of the amino acid sequence or fragment thereof. The amino acid sequence may be 80%, 81%, 82%, 83%, 84%, 85%, 86%, 87%, 88%, 89%, 90%, 91%, 92%, 93%, 94%, 95%, 96%, 97%, 98%, 99%, or 100% identical over the full length of the amino acid sequence or a fragment thereof.

"Vector" as used herein means a nucleic acid sequence containing an origin of replication. A vector can be a viral vector, bacteriophage, bacterial artificial chromosome, or yeast artificial chromosome. A vector can be a DNA or RNA vector. A vector can be a self-replicating extrachromosomal vector, and preferably, is a DNA plasmid. The vector can contain or include one or more heterologous nucleic acid sequences.

Vaccine

Provided herein are vaccines comprising a mesothelin antigen or a nucleic acid molecule encoding a mesothelin antigen as described herein. In some embodiments, the vaccines comprise one or more nucleic acid molecules that encode a mesothelin antigen as described herein. In some embodiments, the vaccines comprise one or more nucleic acid molecules that comprise a nucleic acid sequence that encodes amino acids 19-607 of SEQ ID NO: 2; a nucleic acid sequence that encodes a fragment comprising at least 90% of an entire length of a protein comprising amino acids 19-607 of SEQ ID NO: 2; a nucleic acid sequence that encodes a protein that is at least 96% identical to amino acids 19-607 of SEQ ID NO: 2; and/or a nucleic acid sequence that encodes a fragment comprising at least 90% of an entire length of a protein that is at least 96% identical to amino acids 19-607 of SEQ ID NO: 2.

In some embodiments, the vaccines comprise one or more nucleic acid molecules that comprise a nucleic acid sequence that encodes SEQ ID NO: 2; a nucleic acid sequence that encodes a fragment comprising at least 90% of the length of SEQ ID NO 2; a nucleic acid sequence that encodes a protein that is at least 96% identical to SEQ ID NO: 2; and/or a nucleic acid sequence that encodes a fragment comprising at least 90% of an entire length of a protein that is at least 96% identical to SEQ ID NO: 2.

In some embodiments, the vaccines comprise one or more nucleic acid molecules that comprise nucleotides 55-1821 SEQ ID NO: 1; a fragment comprising at least 90% an entire length of a nucleic acid molecule comprising nucleotides 55-1821 of SEQ ID NO: 1; a fragment that is at least 96% identical to nucleotides 55-1821 of SEQ ID NO: 1; and/or a fragment comprising at least 90% of an entire length of a nucleic acid sequence that is at least 96% identical to nucleotides 55-1821 of SEQ ID NO: 1.

In some embodiments, the vaccines comprise one or more nucleic acid molecules that comprise SEQ ID NO: 1; a fragment comprising at least 90% of the entire length of SEQ ID NO: 1; a fragment that is at least 96% identical to SEQ ID NO: 1; and/or a fragment comprising at least 90% of the entire length of a nucleic acid sequence that is at least 96% identical to SEQ ID NO: 1.

In some embodiments, the vaccine comprises a MUC16 antigen, wherein the antigen comprises amino acids 19-607 of SEQ ID NO: 2; a fragment comprising at least 90% of an entire length of a protein comprising amino acids 19-607 of SEQ ID NO: 2; an amino acid sequence that is at least 95% identical to amino acids 19-607 of SEQ ID NO: 2; and/or a fragment comprising at least 90% of an entire length of an amino acid sequence that is at least 95% identical to amino acids 19-607 of SEQ ID NO: 2.

In some embodiments, the vaccine comprises a MUC16 antigen, wherein the antigen comprises SEQ ID NO: 2; a fragment comprising at least 90% of the length of SEQ ID NO 2; an amino acid sequence that is at least 96% identical to SEQ ID NO: 2; and/or a fragment comprising at least 90% of an entire length of a protein that is at least 96% identical to SEQ ID NO: 2.

The vaccines can be capable of generating in a subject an immune response against the antigen. The immune response can be a therapeutic or prophylactic immune response. The vaccines can be used to protect against cancer, for example, a cancer or tumor expressing mesothelin. The vaccines can be used to prevent and/or treat a tumor expressing mesothelin in a subject in need thereof. The vaccines can induce cellular and/or antibody responses against mesothelin and against tumors expressing mesothelin. In one embodiment, the vaccines can be used to protect against, to prevent and/or treat, or to induce a cellular and/or antibody response against ovarian cancer cells expressing mesothelin, specifically epithelial ovarian cancer cells expressing mesothelin, more specifically serous ovarian cancer cells expressing mesothelin.

The development of a cancer vaccine as described herein comprises identifying a cancer antigen, e.g., mesothelin, that is not recognized by the immune system and is an aberrantly expressed self-antigen. The cancer antigen identified is changed from a self-antigen to a foreign antigen in order to be recognized by the immune system. The redesign of the nucleic acid and amino acid sequences of the recombinant cancer antigen from a self to a foreign antigen breaks tolerance of the antigen by the immune system. In order to break tolerance, several redesign measures can be applied to the cancer antigen as described below.

The recombinant cancer antigen of the vaccine is not recognized as self, thereby breaking tolerance. The breaking of tolerance can induce antigen-specific T cell and/or high titer antibody responses, thereby inducing or eliciting an immune response that is directed to or reactive against the cancer or tumor expressing the antigen. In some embodiments, the induced or elicited immune response can be a cellular, humoral, or both cellular and humoral immune responses. In some embodiments, the induced or elicited cellular immune response can include induction or secretion of interferon-gamma (IFN-γ) and/or tumor necrosis factor alpha (TNF-α). In other embodiments, the induced or elicited immune response can reduce or inhibit one or more immune suppression factors that promote growth of the tumor or cancer expressing the antigen, for example, but not limited to, factors that downregulate MHC presentation, factors that upregulate antigen-specific regulatory T cells (Tregs), PD-L1, FasL, cytokines such as IL-10 and TFG-β, tumor associated macrophages, tumor associated fibroblasts, soluble factors produced by immune suppressor cells, CTLA-4, PD-1, MDSCs, MCP-1, and an immune checkpoint molecule.

The vaccine can be a DNA vaccine. DNA vaccines are disclosed in U.S. Pat. Nos. 5,593,972, 5,739,118, 5,817,637, 5,830,876, 5,962,428, 5,981,505, 5,580,859, 5,703,055, and 5,676,594, which are incorporated herein fully by reference. In some embodiments, the nucleic acid molecule may comprise an expression vector. The DNA vaccine can further comprise elements or reagents that inhibit it from integrating into the chromosome.

The vaccine can include an RNA encoding the cancer antigen. The RNA vaccine can be introduced into the cell.

The vaccine can be an attenuated live vaccine, a vaccine using recombinant vectors to deliver antigen, subunit vaccines, and glycoprotein vaccines, for example, but not limited to, the vaccines described in U.S. Pat. Nos. 4,510, 245; 4,797,368; 4,722,848; 4,790,987; 4,920,209; 5,017, 487; 5,077,044; 5,110,587; 5,112,749; 5,174,993; 5,223, 424; 5,225,336; 5,240,703; 5,242,829; 5,294,441; 5,294, 548; 5,310,668; 5,387,744; 5,389,368; 5,424,065; 5,451, 499; 5,453,364; 5,462,734; 5,470,734; 5,474,935; 5,482, 713; 5,591,439; 5,643,579; 5,650,309; 5,698,202; 5,955, 088; 6,034,298; 6,042,836; 6,156,319 and 6,589,529, which are each incorporated herein by reference.

In some embodiments, the nucleic acid vaccine may further comprise a molecular adjuvant, in some cases the molecular adjuvant can be IL-12, IL-15, IL-28, IL-31, IL-33, and/or RANTES, and in some cases the molecular adjuvant is a checkpoint inhibitor, including anti-cytotoxic T-lymphocyte antigen 4 (CTLA-4), anti-programmed death receptor-1 (PD-1) and anti-lymphocyte-activation gene (LAG-3). Coding sequence for IL-12, IL-15, IL-28, and/or RANTES may be included on one or more nucleic acid molecules that comprise coding sequence for one or more antigens. Coding sequence for IL-12, IL-15, IL-28, IL-31, IL-33, and/or RANTES may be encoded by the nucleic acid vaccine, such as on the same plasmid, or they may be included on separate nucleic acid molecules such as a separate plasmid.

The vaccine of the present invention can have features required of effective vaccines such as being safe so that the vaccine itself does not cause illness or death; being protective against illness; inducing neutralizing antibody; inducing protective T cell responses; and providing ease of administration, few side effects, biological stability, and low cost per dose. The vaccine can accomplish some or all of these features by containing the cancer antigen as discussed below.

The vaccine can further comprise one or more inhibitors of one or more immune checkpoint molecules (i.e., an immune checkpoint inhibitor). Immune checkpoint molecules are described below in more detail. The immune checkpoint inhibitor is any nucleic acid or protein that prevents the suppression of any component in the immune system such as MHC class presentation, T cell presentation and/or differentiation, B cell presentation and/or differentiation, any cytokine, chemokine or signaling for immune cell proliferation and/or differentiation. As also described below in more detail, the vaccine may be combined further with antibodies to checkpoint inhibitors such as PD-1 and PDL-1 to increase the stimulation of both the cellular and humoral immune responses. Using anti-PD-1 or anti-PDL-1 antibodies prevents PD-1 or PDL-1 from suppressing T-cell and/or B-cell responses.

Antigen

As described above, the vaccine can comprise an antigen or a nucleic acid molecule encoding an antigen. The antigen can be mesothelin, a fragment thereof, a variant thereof, or a combination thereof.

Mesothelin is a 71 kD protein that is cleaved into two products: a 30 kD megakaryocyte potentiating factor and 41 kD GPI-anchored membrane-bound mature mesothelin. The function of mesothelin is unknown, however, recent studies suggest that mesothelin may play a role in ovarian cancer metastasis by binding to MUC16, which is also highly expressed on the surface of ovarian cancer cells. Expression of mesothelin has been observed in 82-100% of serous ovarian carcinomas by IHC. Hassan, R. European journal of cancer 44, 46-53 (2008); Ordonez, N. G. The American journal of surgical pathology 27, 1418-1428 (2003).

Accordingly, the vaccine can be used for treating subjects suffering from mesothelin-expressing cancer or tumors. In some embodiments, the cancer is ovarian cancer. The mesothelin antigen can differ from the native, "normal" mesothelin, and thus provide therapy or prophylaxis against a mesothelin antigen-expressing tumor. Accordingly, mesothelin antigen sequences that differ from the native mesothelin gene (i.e., recombined or mutated mesothelin genes or sequences), are provided herein.

Nucleic acid molecules comprising the above-described heterologous sequences are provided. Nucleic acid molecules consisting of the above-described heterologous sequences are provided. In some embodiments, nucleic acid molecules comprise one or more nucleic acid sequences selected from the group consisting of: (a) nucleotides 55-1821 SEQ ID NO: 1; (b) a fragment comprising at least 90%, 91%, 92%, 93%, 94%, 95%, 96%, 97%, 98% or 99% an entire length of a nucleic acid molecule comprising nucleotides 55-1821 of SEQ ID NO: 1; (c) a fragment that is at least 96%, 97%, 98% or 99% identical to nucleotides 55-1821 of SEQ ID NO: 1; and (d) a fragment comprising at least 90%, 91%, 92%, 93%, 94%, 95%, 96%, 97%, 98% or 99% of an entire length of a nucleic acid sequence that is at least 96%, 97%, 98% or 99% identical to nucleotides 55-1821 of SEQ ID NO: 1. In some embodiments, nucleic acid molecules comprise one or more nucleic acid sequences selected from the group consisting of: (a) SEQ ID NO: 1; (b) a fragment comprising at least 90%, 91%, 92%, 93%, 94%, 95%, 96%, 97%, 98% or 99% of an entire length of SEQ ID NO: 1; (c) a fragment that is at least 96%, 97%, 98% or 99% identical to SEQ ID NO: 1; and (d) a fragment comprising at least 90% of an entire length of a nucleic acid sequence that is at least 96%, 97%, 98% or 99% identical to SEQ ID NO: 1. In some embodiments, the nucleic acid molecule comprises the nucleic acid sequence set forth in SEQ ID NO: 1.

Provided herein are nucleic acid sequences that encode mesothelin antigens. In some embodiments, nucleic acid molecules comprising one or more nucleic acids selected from (a) a nucleic acid sequence that encodes amino acids 19-607 of SEQ ID NO: 2; (b) a nucleic acid sequence that encodes a fragment comprising at least 90%, 91%, 92%, 93%, 94%, 95%, 96%, 97%, 98% or 99% of an entire length of a protein comprising amino acids 19-607 of SEQ ID NO: 2; (c) a nucleic acid sequence that encodes a protein that is at least 96%, 97%, 98% or 99% identical to amino acids 19-607 of SEQ ID NO: 2; and (d) a nucleic acid sequence that encodes a fragment comprising at least 90%, 91%, 92%, 93%, 94%, 95%, 96%, 97%, 98% or 99% of an entire length of a protein that is at least 96%, 97%, 98% or 99% identical to amino acids 19-607 of SEQ ID NO: 2 In some embodiments, nucleic acid molecules comprising one or more nucleic acid sequences selected from the group consisting of: (a) a nucleic acid sequence that encodes SEQ ID NO: 2; (b) a nucleic acid sequence that encodes a fragment comprising at least 90%, 91%, 92%, 93%, 94%, 95%, 96%, 97%, 98% or 99% of an entire length of SEQ ID NO: 2; (c) a nucleic acid sequence that encodes a protein that is at least 96%, 97%, 98% or 99% identical to SEQ ID NO: 2; and (d) a nucleic acid sequence that encodes a fragment comprising at least 90% of an entire length of a protein that is at least 96%, 97%, 98% or 99% identical to SEQ ID NO: 2 are provided.

Isolated nucleic acid molecules comprising the above-described heterologous sequences may be incorporated into vectors such as plasmids, viral vectors and other forms of nucleic acid molecules as described below.

Protein molecules comprising the above described heterologous amino acid sequences are provided. Protein molecules consisting of the above described heterologous amino acid sequences are provided. Provided herein are proteins and polypeptides having the above-described sequences. The proteins and polypeptide may be referred to as mesothelin antigens and mesothelin immunogens. Mesothelin antigens are capable of eliciting an immune response against tumors expressing a mesothelin antigen. In some embodiments, proteins comprising the amino acid sequence selected from the group consisting of: (a) amino acids 19-607 of SEQ ID NO: 2; (b) a fragment comprising at least 90%, 91%, 92%, 93%, 94%, 95%, 96%, 97%, 98% or 99% of an entire length of a protein comprising amino acids 19-607 of SEQ ID NO: 2; (c) an amino acid sequence that is at least 95% identical to amino acids 19-607 of SEQ ID NO: 2; and (d) a fragment comprising at least 90%, 91%, 92%, 93%, 94%, 95%, 96%, 97%, 98% or 99% of an entire length of an amino acid sequence that is at least 96%, 97%, 98% or 99% identical to amino acids 19-607 of SEQ ID NO: 2. In some embodiments, proteins comprising the amino acid sequence selected from the group consisting of: (a) SEQ ID NO: 2; (b) a fragment comprising at least 90%, 91%, 92%, 93%, 94%, 95%, 96%, 97%, 98% or 99% of an entire length of SEQ ID NO: 2; (c) an amino acid sequence that is at least 96%, 97%, 98% or 99% identical to SEQ ID NO: 2; and (c) a fragment comprising at least 90%, 91%, 92%, 93%, 94%, 95%, 96%, 97%, 98% or 99% of an entire length of an amino acid sequence that is at least 96%, 97%, 98% or 99% identical to SEQ ID NO: 2 are provided. In some embodiments, the protein comprises the amino acid sequence set forth in SEQ ID NO: 2.

In one aspect, it is desired that the consensus antigen provides for improved transcription and translation, including having one or more of the following: low GC content leader sequence to increase transcription; mRNA stability and codon optimization; and, to the extent possible, elimination of cis-acting sequence motifs (i.e., internal TATA-boxes).

The mesothelin antigen can be a consensus antigen (or immunogen) sequence derived from two or more species. The mesothelin consensus antigen can comprise one or more mutations which can include a substitution of one or more of the amino acids in the MUC-16 binding domain. The one or more mutations may comprise nucleic acid mutations resulting in a substitution of tyrosine to alanine. The one or more mutations can include a substitution of one or more of the amino acids in the GPI-anchoring signal. The one or more mutations may comprise substitution of serine to threonine and/or threonine to valine. Accordingly, in some embodiments, the one or more mutations can replace 1, 2 or 3 amino acids in the mesothelin MUC16 binding and/or GPI-anchoring signal.

The mesothelin antigen can comprise modifications for improved expression. Modification can include codon optimization, RNA optimization, addition of a kozak sequence (e.g., GCC ACC) for increased translation initiation and/or the addition of an immunoglobulin leader sequence to increase the immunogenicity of the mesothelin antigen. The mesothelin antigen can comprise a signal peptide such as an immunoglobulin signal peptide, for example, but not limited to, an immunoglobulin E (IgE) or immunoglobulin G (IgG) signal peptide.

Vaccine in Combination with Immune Checkpoint Inhibitor

The vaccine can further comprise one or more inhibitors of one or more immune checkpoint molecules (i.e., an immune checkpoint inhibitor). Immune check point molecules are described below in more detail. The immune checkpoint inhibitor is any nucleic acid or protein that prevents the suppression of any component in the immune system such as MHC class presentation, T cell presentation and/or differentiation, B cell presentation and/or differentiation, any cytokine, chemokine or signaling for immune cell proliferation and/or differentiation.

Such an inhibitor can be a nucleic acid sequence, an amino acid sequence, a small molecule, or a combination thereof. The nucleic acid sequence can be DNA, RNA, cDNA, a variant thereof, a fragment thereof, or a combination thereof. The nucleic acid can also include additional sequences that encode linker or tag sequences that are linked to the immune checkpoint inhibitor by a peptide bond. The small molecule may be a low molecular weight, for example, less than 800 Daltons, organic or inorganic compound that can serve as an enzyme substrate, ligand (or analog thereof) bound by a protein or nucleic acid, or regulator of a biological process. The amino acid sequence can be protein, a peptide, a variant thereof, a fragment thereof, or a combination thereof.

In some embodiments, the immune checkpoint inhibitor can be one or more nucleic acid sequences encoding an antibody, a variant thereof, a fragment thereof, or a combination thereof. In other embodiments, the immune check point inhibitor can be an antibody, a variant thereof, a fragment thereof, or a combination thereof.

a. Immune Checkpoint Molecule

The immune check point molecule can be a nucleic acid sequence, an amino acid sequence, a small molecule, or a combination thereof. The nucleic acid sequence can be DNA, RNA, cDNA, a variant thereof, a fragment thereof, or a combination thereof. The nucleic acid can also include additional sequences that encode linker or tag sequences that are linked to the immune checkpoint inhibitor by a peptide bond. The small molecule may be a low molecular weight, for example, less than 800 Daltons, organic or inorganic compound that can serve as an enzyme substrate, ligand (or analog thereof) bound by a protein or nucleic acid, or regulator of a biological process. The amino acid sequence can be protein, a peptide, a variant thereof, a fragment thereof, or a combination thereof.

(1) PD-1 and PD-L1

The immune checkpoint molecule may programmed cell death protein 1 (PD-1), programmed cell death ligand 1 (PD-L1), a fragment thereof, a variant thereof, or a combination thereof. PD-1 is a cell surface protein encoded by the PDCD1 gene. PD-1 is a member of the immunoglobulin superfamily and is expressed on T cells and pro-B cells, and thus, contributes to the fate and/or differentiation of these cells. In particular, PD-1 is a type 1 membrane protein of the CD28/CTLA-4 family of T cell regulators and negatively regulates T cell receptor (TCR) signals, thereby negatively regulating immune responses. PD-1 can negatively regulated CD8+ T cell responses, and thus inhibit CD8-mediated cytotoxicity and enhance tumor growth.

PD-1 has two ligands, PD-L1 and PD-L2, which are members of the B7 family. PD-L1 is upregulated on macrophages and dendritic cells (DCs) in response to LPS and GM-CSF treatment and onn T cells and B cells upon TCR and B cell receptor signaling. PD-L1 is expressed by many tumor cell lines, including myelomas, mastocytomas, and melanomas.

b. Anti-Immune Checkpoint Molecule Antibody

As described above, the immune checkpoint inhibitor can be an antibody. The antibody can bind or react with an antigen (i.e., the immune checkpoint molecule described above.) Accordingly, the antibody may be considered an anti-immune checkpoint molecule antibody or an immune checkpoint molecule antibody. The antibody can be encoded by a nucleic acid sequence contained in The antibody can include a heavy chain polypeptide and a light chain polypeptide. The heavy chain polypeptide can include a variable heavy chain (VH) region and/or at least one constant heavy chain (CH) region. The at least one constant heavy chain region can include a constant heavy chain region 1 (CH1), a constant heavy chain region 2 (CH2), and a constant heavy chain region 3 (CH3), and/or a hinge region.

In some embodiments, the heavy chain polypeptide can include a VH region and a CH1 region. In other embodiments, the heavy chain polypeptide can include a VH region, a CH1 region, a hinge region, a CH2 region, and a CH3 region.

The heavy chain polypeptide can include a complementarity determining region ("CDR") set. The CDR set can contain three hypervariable regions of the VH region. Proceeding from N-terminus of the heavy chain polypeptide, these CDRs are denoted "CDR1," "CDR2," and "CDR3," respectively. CDR1, CDR2, and CDR3 of the heavy chain polypeptide can contribute to binding or recognition of the antigen.

The light chain polypeptide can include a variable light chain (VL) region and/or a constant light chain (CL) region. The light chain polypeptide can include a complementarity determining region ("CDR") set. The CDR set can contain three hypervariable regions of the VL region. Proceeding from N-terminus of the light chain polypeptide, these CDRs are denoted "CDR1," "CDR2," and "CDR3," respectively. CDR1, CDR2, and CDR3 of the light chain polypeptide can contribute to binding or recognition of the antigen.

The antibody may comprise a heavy chain and a light chain complementarity determining region ("CDR") set, respectively interposed between a heavy chain and a light chain framework ("FR") set which provide support to the CDRs and define the spatial relationship of the CDRs relative to each other. The CDR set may contain three hypervariable regions of a heavy or light chain V region. Proceeding from the N-terminus of a heavy or light chain, these regions are denoted as "CDR1," "CDR2," and "CDR3," respectively. An antigen-binding site, therefore, may include six CDRs, comprising the CDR set from each of a heavy and a light chain V region.

The antibody can be an immunoglobulin (Ig). The Ig can be, for example, IgA, IgM, IgD, IgE, and IgG. The immunoglobulin can include the heavy chain polypeptide and the light chain polypeptide. The heavy chain polypeptide of the immunoglobulin can include a VH region, a CH1 region, a hinge region, a CH2 region, and a CH3 region. The light chain polypeptide of the immunoglobulin can include a VL region and CL region.

Additionally, the proteolytic enzyme papain preferentially cleaves IgG molecules to yield several fragments, two of which (the F(ab) fragments) each comprise a covalent heterodimer that includes an intact antigen-binding site. The enzyme pepsin is able to cleave IgG molecules to provide several fragments, including the F(ab')2 fragment, which comprises both antigen-binding sites. Accordingly, the antibody can be the Fab or F(ab')2. The Fab can include the heavy chain polypeptide and the light chain polypeptide. The heavy chain polypeptide of the Fab can include the VH region and the CH1 region. The light chain of the Fab can include the VL region and CL region.

The antibody can be a polyclonal or monoclonal antibody. The antibody can be a chimeric antibody, a single chain antibody, an affinity matured antibody, a human antibody, a humanized antibody, or a fully human antibody. The humanized antibody can be an antibody from a non-human species that binds the desired antigen having one or more complementarity determining regions (CDRs) from the non-human species and framework regions from a human immunoglobulin molecule.

(1) PD-1 Antibody

The anti-immune checkpoint molecule antibody can be an anti-PD-1 antibody (also referred to herein as "PD-1 antibody"), a variant thereof, a fragment thereof, or a combination thereof. The PD-1 antibody can be Nivolumab. The anti-PD-1 antibody can inhibit PD-1 activity, thereby inducing, eliciting, or increasing an immune response against a tumor or cancer and decreasing tumor growth.

(2) PD-L1 Antibody

The anti-immune checkpoint molecule antibody can be an anti-PD-L1 antibody (also referred to herein as "PD-L1 antibody"), a variant thereof, a fragment thereof, or a combination thereof. The anti-PD-L1 antibody can inhibit PD-L1 activity, thereby inducing, eliciting, or increasing an immune response against a tumor or cancer and decreasing tumor growth.

Vector

The vaccine can comprise one or more vectors that include a heterologous nucleic acid encoding the mesothelin antigen. The one or more vectors can be capable of expressing the antigen in a quantity effective to elicit an immune response in the mammal. The vector may comprise heterologous nucleic acid encoding the antigen. The vector can have a nucleic acid sequence containing an origin of replication. The vector can be a plasmid, bacteriophage, bacterial artificial chromosome or yeast artificial chromosome. The vector can be either a self-replicating extra chromosomal vector or a vector which integrates into a host genome.

The one or more vectors can be an expression construct, which is generally a plasmid that is used to introduce a specific gene into a target cell. Once the expression vector is inside the cell, the protein that is encoded by the gene is produced by the cellular-transcription and translation machinery ribosomal complexes. The plasmid is frequently engineered to contain regulatory sequences that act as enhancer and promoter regions and lead to efficient transcription of the gene carried on the expression vector. The vectors of the present invention express large amounts of stable messenger RNA, and therefore proteins.

The vectors may have expression signals such as a strong promoter, a strong termination codon, adjustment of the distance between the promoter and the cloned gene, and the insertion of a transcription termination sequence and a PTIS (portable translation initiation sequence).

The vectors may comprise nucleic acid sequences operably linked to a regulatory element selected from a promoter and a poly-adenylation signal. In some embodiments, the promoter is a human cytomegalovirus immediate-early promoter (hCMV promoter). In some embodiments, the polyadenylation signal is a bovine growth hormone poly-adenylation signal (bGH polyA).

The vector can be a circular plasmid or a linear nucleic acid. The circular plasmid and linear nucleic acid are capable of directing expression of a particular nucleotide sequence in an appropriate subject cell. The vector can have a promoter operably linked to the antigen-encoding nucleotide sequence, which may be operably linked to termination signals. The vector can also contain sequences required for proper translation of the nucleotide sequence as well as sequences for cloning and subcloning the vector and fragments thereof. The vector comprising the nucleotide sequence of interest may be chimeric, meaning that at least one of its components is heterologous with respect to at least one of its other components. The expression of the nucleotide sequence in the expression cassette may be under the control of a constitutive promoter or of an inducible promoter, which initiates transcription only when the host cell is exposed to some particular external stimulus. In the case of a multicellular organism, the promoter can also be specific to a particular tissue or organ or stage of development.

The vector can be a plasmid. The plasmid may be useful for transfecting cells with nucleic acid encoding the antigen, which the transformed host cells is cultured and maintained under conditions wherein expression of the antigen takes place.

The plasmid may comprise a nucleic acid sequence that encodes one or more of the various antigens disclosed above including coding sequences that encode synthetic, consensus antigen capable of eliciting an immune response against an antigen, fragments of such proteins, variants of such proteins, fragments of variants or fusion proteins which are made up of combinations of consensus proteins and/or fragments of consensus protein and/or variants of consensus protein and/or fragments of variants consensus proteins.

In some embodiments, a plasmid may further comprise coding sequence that encodes CCR20 alone or as part of one these plasmids. Similarly, plasmids may further comprise coding sequences for IL-12, IL-15 and/or IL-28.

The plasmid may further comprise an initiation codon, which may be upstream of the coding sequence, and a stop codon, which may be downstream of the coding sequence. The initiation and termination codon may be in frame with the coding sequence.

The plasmid may also comprise a promoter that is operably linked to the coding sequence. The promoter operably linked to the coding sequence may be a promoter from simian virus 40 (SV40), a mouse mammary tumor virus (MMTV) promoter, a human immunodeficiency virus (HIV) promoter such as the bovine immunodeficiency virus (BIV) long terminal repeat (LTR) promoter, a Moloney virus promoter, an avian leukosis virus (ALV) promoter, a cytomegalovirus (CMV) promoter such as the CMV immediate-early promoter (hCMV promoter), Epstein Barr virus (EBV) promoter, or a Rous sarcoma virus (RSV) promoter. The promoter may also be a promoter from a human gene such as human actin, human myosin, human hemoglobin, human muscle creatine, or human metalothionein. The promoter may also be a tissue specific promoter, such as a muscle or skin specific promoter, natural or synthetic. Examples of such promoters are described in US patent application publication no. US20040175727, the contents of which are incorporated herein in its entirety.

The plasmid may also comprise a polyadenylation signal, which may be downstream of the coding sequence. The polyadenylation signal may be a SV40 polyadenylation signal, LTR polyadenylation signal, bovine growth hormone (bGH) polyadenylation signal, human growth hormone (hGH) polyadenylation signal, human β-globin polyadenylation signal or a bovine growth hormone poly-adenylation signal (bGH polyA). The SV40 polyadenylation signal may be a polyadenylation signal from a pCEP4 plasmid (Invitrogen, San Diego, Calif.).

The plasmid may also comprise an enhancer upstream of the coding sequence. The enhancer may be human actin, human myosin, human hemoglobin, human muscle creatine or a viral enhancer such as one from CMV, FMDV, RSV or EBV. Polynucleotide function enhances are described in U.S. Pat. Nos. 5,593,972, 5,962,428, and WO94/016737, the contents of each are fully incorporated by reference.

The plasmid may also comprise a mammalian origin of replication in order to maintain the plasmid extrachromosomally and produce multiple copies of the plasmid in a cell. The plasmid may be p V AXI, pCEP4 or pREP4 from Invitrogen (San Diego, Calif.), which may comprise the Epstein Barr virus origin of replication and nuclear antigen EBNA-1 coding region, which may produce high copy episomal replication without integration. The backbone of the plasmid may be pA V0242. The plasmid may be a replication defective adenovirus type 5 (Ad5) plasmid.

The plasmid may also comprise a regulatory sequence, which may be well suited for gene expression in a cell into which the plasmid is administered. The coding sequence may comprise a codon that may allow more efficient transcription of the coding sequence in the host cell.

The coding sequence may also comprise an immunoglobulin (Ig) leader sequence. The leader sequence may be 5" of the coding sequence. The consensus antigens encoded by this sequence may comprise an N-terminal Ig leader followed by a consensus antigen protein. The N-terminal Ig leader may be IgE or IgG.

The plasmid may be pSE420 (Invitrogen, San Diego, Calif.), which may be used for protein production in *Escherichia coli* (*E. coli*). The plasmid may also be p-YES2 (Invitrogen, San Diego, Calif.), which may be used for protein production in *Saccharomyces cerevisiae* strains of yeast. The plasmid may also be of the MAXBAC™ complete baculovirus expression system (Invitrogen, San Diego, Calif.), which may be used for protein production in insect cells. The plasmid may also be pcDNA I or pcDNA3 (Invitrogen, San Diego, Calif.), which may be used for protein production in mammalian cells such as Chinese hamster ovary (CHO) cells. The plasmid may also be pGX001 (Inovio), which is modified from pVAX1 (Thermo Fisher Scientific, Waltham, Mass.).

The vector may be circular plasmid, which may transform a target cell by integration into the cellular genome or exist extrachromosomally (e.g., autonomous replicating plasmid with an origin of replication).

The vector can be pVAX, pcDNA3.0, or provax, or any other expression vector capable of expressing DNA encoding the antigen and enabling a cell to translate the sequence to an antigen that is recognized by the immune system.

Also provided herein is a linear nucleic acid vaccine, or linear expression cassette ("LEC"), that is capable of being efficiently delivered to a subject via electroporation and expressing one or more desired antigens. The LEC may be any linear DNA devoid of any phosphate backbone. The DNA may encode one or more antigens. The LEC may contain a promoter, an intron, a stop codon, and/or a polyadenylation signal. The expression of the antigen may be controlled by the promoter. The LEC may not contain any antibiotic resistance genes and/or a phosphate backbone. The LEC may not contain other nucleic acid sequences unrelated to the desired antigen gene expression.

The LEC may be derived from any plasmid capable of being linearized. The plasmid may be capable of expressing the antigen. The plasmid can be pNP (Puerto Rico/34) or pM2 (New Caledonia/99). The plasmid may be WLV009, pVAX, pcDNA3.0, or provax, or any other expression vector capable of expressing DNA encoding the antigen and enabling a cell to translate the sequence to an antigen that is recognized by the immune system.

The LEC can be perM2. The LEC can be perNP. perNP and perMR can be derived from pNP (Puerto Rico/34) and pM2 (New Caledonia/99), respectively.

The vector may have a promoter. A promoter may be any promoter that is capable of driving gene expression and regulating expression of the isolated nucleic acid. Such a promoter is a cis-acting sequence element required for transcription via a DNA dependent RNA polymerase, which transcribes the antigen sequence described herein. Selection of the promoter used to direct expression of a heterologous nucleic acid depends on the particular application. The promoter may be positioned about the same distance from the transcription start in the vector as it is from the transcription start site in its natural setting. However, variation in this distance may be accommodated without loss of promoter function.

The promoter may be operably linked to the nucleic acid sequence encoding the antigen and signals required for efficient polyadenylation of the transcript, ribosome binding sites, and translation termination.

The promoter may be a CMV promoter, SV40 early promoter, SV40 later promoter, metallothionein promoter, murine mammary tumor virus promoter, Rous sarcoma virus promoter, polyhedrin promoter, or another promoter shown effective for expression in eukaryotic cells.

The vector may include an enhancer and an intron with functional splice donor and acceptor sites. The vector may contain a transcription termination region downstream of the structural gene to provide for efficient termination. The termination region may be obtained from the same gene as the promoter sequence or may be obtained from different genes.

Methods of Preparing the Vector

Provided herein are methods for preparing the vector that comprises the nucleic acid molecules encoding mesothelin antigen discussed herein. The vector, after the final subcloning step into the mammalian expression plasmid, can be used to inoculate a cell culture in a large scale fermentation tank, using known methods in the art.

The vector for use with the electroporation devices, which are described below in more detail, can be formulated or manufactured using a combination of known devices and techniques, but preferably they are manufactured using an optimized plasmid manufacturing technique that is described in a US Publication No. 2009/004716, which was filed on May 23, 2008. In some examples, the DNA plasmids used in these studies can be formulated at concentrations greater than or equal to 10 mg/mL. The manufacturing techniques also include or incorporate various devices and protocols that are commonly known to those of ordinary skill in the art, in addition to those described in U.S. Ser. No. 60/939,792, including those described in U.S. Pat. No. 7,238,522, which issued on Jul. 3, 2007. The above-referenced publication and patent, US Publication No. 2009/004716 and U.S. Pat. No. 7,238,522, respectively, are hereby incorporated in their entirety.

Excipients and Other Components of the Vaccine

The vaccine may further comprise a pharmaceutically acceptable excipient. The pharmaceutically acceptable excipient can be functional molecules such as vehicles, carriers, or diluents. The pharmaceutically acceptable excipient can be a transfection facilitating agent, which can include surface active agents, such as immune-stimulating complexes (ISCOMS), Freunds incomplete adjuvant, LPS analog including monophosphoryl lipid A, muramyl peptides, quinone analogs, vesicles such as squalene and squalene, hyaluronic acid, lipids, liposomes, calcium ions, viral proteins, polyanions, polycations, or nanoparticles, or other known transfection facilitating agents.

The transfection facilitating agent is a polyanion, polycation, including poly-L-glutamate (LGS), or lipid. The transfection facilitating agent is poly-L-glutamate, and the poly-L-glutamate may be present in the vaccine at a concentration less than 6 mg/ml. The transfection facilitating agent may also include surface active agents such as immune-stimulating complexes (ISCOMS), Freunds incomplete adjuvant, LPS analog including monophosphoryl lipid A, muramyl peptides, quinone analogs and vesicles such as squalene and squalene, and hyaluronic acid may also be used administered in conjunction with the genetic construct. The DNA plasmid vaccines may also include a transfection facilitating agent such as lipids, liposomes, including lecithin liposomes or other liposomes known in the art, as a DNA-liposome mixture (see for example WO9324640), calcium ions, viral proteins, polyanions, polycations, or nanoparticles, or other known transfection facilitating agents. The transfection facilitating agent is a polyanion, polycation, including poly-L-glutamate (LGS), or lipid. Concentration of the transfection agent in the vaccine is less than 4 mg/ml, less than 2 mg/ml, less than 1 mg/ml, less than 0.750 mg/ml, less than 0.500 mg/ml, less than 0.250 mg/ml, less than 0.100 mg/ml, less than 0.050 mg/ml, or less than 0.010 mg/ml.

The pharmaceutically acceptable excipient can be one or more adjuvants. The adjuvant can be other genes that are expressed in an alternative plasmid or are delivered as proteins in combination with the plasmid above in the vaccine. The one or more adjuvants may be selected from the group consisting of: CCL20, α-interferon (IFN-α), β-interferon (IFN-β), γ-interferon, platelet derived growth factor (PDGF), TNFα, TNFβ, GM-CSF, epidermal growth factor (EGF), cutaneous T cell-attracting chemokine (CTACK), epithelial thymus-expressed chemokine (TECK), mucosae-associated epithelial chemokine (MEC), IL-12, IL-15, IL-28, IL-31, IL-33, MHC, CD80, CD86, IL-1, IL-2, IL-4, IL-5, IL-6, IL-10, IL-18, MCP-1, MIP-1a, MIP-1~, IL-8, L-selectin, P-selectin, E-selectin, CD34, GlyCAM-1, MadCAM-1, LFA-1, VLA-1, Mac-1, p150.95, PECAM, ICAM-1, ICAM-2, ICAM-3, CD2, LFA-3, M-CSF, G-CSF, mutant forms of IL-18, CD40, CD40L, vascular growth factor, fibroblast growth factor, IL-7, nerve growth factor, vascular endothelial growth factor, Fas, TNF receptor, Flt, Apo-1, p55, WSL-1, DR3, TRAMP, Apo-3, AIR, LARD, NGRF, DR4, DR5, KILLER, TRAIL-R2, TRICK2, DR6, Caspase ICE, Fos, c-jun, Sp-1, Ap-1, Ap-2, p38, p65Rel, MyD88, IRAK, TRAF6, IkB, Inactive NIK, SAP K, SAP-I, JNK, interferon response genes, NFkB, Bax, TRAIL, TRAILrec, TRAILrecDRC5, TRAIL-R3, TRAIL-R4, RANK, RANK LIGAND, Ox40, Ox40 LIGAND, NKG2D, MICA, MICB, NKG2A, NKG2B, NKG2C, NKG2E, NKG2F, TAP1, TAP2, IL-15 having the signal sequence or coding sequence that encodes the signal sequence deleted and optionally including a different signal peptide such as that from IgE or coding sequence that encodes a different signal peptide such as that from IgE, and functional fragments thereof, or a combination thereof. The adjuvant can be IL-12, IL-15, IL-28, CTACK, TECK, platelet derived growth factor (PDGF), TNFα, TNFβ, GM-CSF, epidermal growth factor (EGF), IL-1, IL-2, IL-4, IL-5, IL-6, IL-10, IL-12, IL-18, or a combination thereof.

In some embodiments the adjuvant may be one or more proteins and/or nucleic acid molecules that encode proteins selected from the group consisting of: CCL-20, IL-12, IL-15, IL-28, CTACK, TECK, MEC or RANTES. Examples of IL-12 constructs and sequences are disclosed in PCT application no. PCT/US1997/019502 and corresponding U.S. application Ser. No. 08/956,865, and U.S. Provisional Application Ser. No. 61/569,600 filed Dec. 12, 2011, which are each incorporated herein by reference. Examples of IL-15 constructs and sequences are disclosed in PCT application no. PCT/US04/18962 and corresponding U.S. application Ser. No. 10/560,650, and in PCT application no. PCT/US07/00886 and corresponding U.S. application Ser. No. 12/160,766, and in PCT application no. PCT/USI0/048827, which are each incorporated herein by reference. Examples of IL-28 constructs and sequences are disclosed in PCT application no. PCT/US09/039648 and corresponding U.S. application Ser. No. 12/936,192, which are each incorporated herein by reference. Examples of RANTES and other constructs and sequences are disclosed in PCT application no. PCT/US1999/004332 and corresponding U.S. application Ser. No. 09/622,452, which are each incorporated herein by reference. Other examples of RANTES constructs and sequences are disclosed in PCT application no. PCT/US11/024098, which is incorporated herein by reference. Examples of RANTES and other constructs and sequences are disclosed in PCT application no. PCT/US1999/004332 and corresponding U.S. application Ser. No. 09/622,452, which are each incorporated herein by reference. Other examples of RANTES constructs and sequences are disclosed in PCT application no. PCT/US11/024098, which is incorporated herein by reference. Examples of chemokines CTACK, TECK and MEC constructs and sequences are disclosed in PCT application no. PCT/US2005/042231 and corresponding U.S. application Ser. No. 11/719,646, which are each incorporated herein by reference. Examples of OX40 and other immunomodulators are disclosed in U.S. application Ser. No. 10/560,653, which is incorporated herein by reference. Examples of DR5 and other immunomodulators are disclosed in U.S. application Ser. No. 09/622,452, which is incorporated herein by reference.

Other genes that can be useful as adjuvants include those encoding: MCP-1, MIP-1a, MIP-1p, IL-8, RANTES, L-selectin, P-selectin, E-selectin, CD34, GlyCAM-1, MadCAM-1, LFA-1, VLA-1, Mac-1, p150.95, PECAM, ICAM-1, ICAM-2, ICAM-3, CD2, LFA-3, M-CSF, G-CSF, IL-4, mutant forms of IL-18, CD40, CD40L, vascular growth factor, fibroblast growth factor, IL-7, IL-22, nerve growth factor, vascular endothelial growth factor, Fas, TNF receptor, Flt, Apo-1, p55, WSL-1, DR3, TRAMP, Apo-3, AIR, LARD, NGRF, DR4, DR5, KILLER, TRAIL-R2, TRICK2, DR6, Caspase ICE, Fos, c-jun, Sp-1, Ap-1, Ap-2, p38, p65Rel, MyD88, IRAK, TRAF6, IkB, Inactive NIK, SAP K, SAP-1, JNK, interferon response genes, NFkB, Bax, TRAIL, TRAILrec, TRAILrecDRC5, TRAIL-R3, TRAIL-R4, RANK, RANK LIGAND, Ox40, Ox40 LIGAND, NKG2D, MICA, MICB, NKG2A, NKG2B, NKG2C, NKG2E, NKG2F, TAP1, TAP2 and functional fragments thereof.

The vaccine may further comprise a genetic vaccine facilitator agent as described in U.S. Ser. No. 021,579 filed Apr. 1, 1994, which is fully incorporated by reference.

The vaccine may comprise the antigen-encoding vector at quantities of from about 1 nanogram to 100 milligrams; about 1 microgram to about 10 milligrams; or preferably about 0.1 microgram to about 10 milligrams; or more preferably about 1 milligram to about 2 milligram. In some preferred embodiments, vaccine according to the present invention comprise about 5 nanogram to about 1000 micrograms of nucleic acid. In some preferred embodiments, vaccine can contain about 10 nanograms to about 800 micrograms of nucleic acid. In some preferred embodiments, the vaccine can contain about 0.1 to about 500 micrograms of nucleic acid. In some preferred embodiments, the vaccine can contain about 1 to about 350 micrograms of nucleic acid. In some preferred embodiments, the vaccine can contain about 25 to about 250 micrograms, from about 100 to about 200 microgram, from about 1 nanogram to 100 milligrams; from about 1 microgram to about 10 milligrams; from about 0.1 microgram to about 10 milligrams; from about 1 milligram to about 2 milligram, from about 5 nanogram to about 1000 micrograms, from about 10 nanograms to about 800 micrograms, from about 0.1 to about 500 micrograms, from about 1 to about 350 micrograms, from about 25 to about 250 micrograms, from about 100 to about 200 microgram of the antigen or plasmid thereof.

The vaccine can be formulated according to the mode of administration to be used. An injectable vaccine pharmaceutical composition can be sterile, pyrogen free and particulate free. An isotonic formulation or solution can be used. Additives for isotonicity can include sodium chloride, dextrose, mannitol, sorbitol, and lactose. The vaccine can comprise a vasoconstriction agent. The isotonic solutions can include phosphate buffered saline. Vaccine can further comprise stabilizers including gelatin and albumin. The stabilizers can allow the formulation to be stable at room or ambient temperature for extended periods of time, including LGS or polycations or polyanions.

Pharmaceutical Compositions of the Vaccine

The vaccine can be in the form of a pharmaceutical composition. The pharmaceutical composition can comprise the vaccine. The pharmaceutical compositions can comprise about 5 nanograms (ng) to about 10 milligrams (mg) of the nucleic acid molecule of the vaccine. In some embodiments, pharmaceutical compositions according to the present invention comprise about 25 ng to about 5 mg of the nucleic acid molecule of the vaccine. In some embodiments, the pharmaceutical compositions contain about 50 ng to about 1 mg of the nucleic acid molecule of the vaccine. In some embodiments, the pharmaceutical compositions contain about 0.1 to about 500 micrograms of the nucleic acid molecule of the vaccine. In some embodiments, the pharmaceutical compositions contain about 1 to about 350 micrograms of the nucleic acid molecule of the vaccine. In some embodiments, the pharmaceutical compositions contain about 5 to about 250 micrograms of the nucleic acid molecule of the vaccine. In some embodiments, the pharmaceutical compositions contain about 10 to about 200 micrograms of the nucleic acid molecule of the vaccine. In some embodiments, the pharmaceutical compositions contain about 15 to about 150 micrograms of the nucleic acid molecule of the vaccine. In some embodiments, the pharmaceutical compositions contain about 20 to about 100 micrograms of the nucleic acid molecule of the vaccine. In some embodiments, the pharmaceutical compositions contain about 25 to about 75 micrograms of the nucleic acid molecule of the vaccine. In some embodiments, the pharmaceutical compositions contain about 30 to about 50 micrograms of the nucleic acid molecule of the vaccine. In some embodiments, the pharmaceutical compositions contain about 35 to about 40 micrograms of the nucleic acid molecule of the vaccine. In some embodiments, the pharmaceutical compositions contain about 100 to about 200 micrograms of the nucleic acid molecule of the vaccine. In some embodiments, the pharmaceutical compositions comprise about 10 micrograms to about 100 micrograms of the nucleic acid molecule of the vaccine. In some embodiments, the pharmaceutical compositions comprise about 20 micrograms to about 80 micrograms of the nucleic acid molecule of the vaccine. In some embodiments, the pharmaceutical compositions comprise about 25 micrograms to about 60 micrograms of the nucleic acid molecule of the vaccine. In some embodiments, the pharmaceutical compositions comprise about 30 ng to about 50 micrograms of the nucleic acid molecule of the vaccine. In some embodiments, the pharmaceutical compositions comprise about 35 ng to about 45 micrograms of the nucleic acid molecule of the vaccine. In some preferred embodiments, the pharmaceutical compositions contain about 0.1 to about 500 micrograms of the nucleic acid molecule of the vaccine. In some preferred embodiments, the pharmaceutical compositions contain about 1 to about 350 micrograms of the nucleic acid molecule of the vaccine. In some preferred embodiments, the pharmaceutical compositions contain about 25 to about 250 micrograms of the nucleic acid molecule of the vaccine. In some preferred embodiments, the pharmaceutical compositions contain about 100 to about 200 micrograms of the nucleic acid molecule of the vaccine.

In some embodiments, pharmaceutical compositions according to the present invention comprise at least 10, 15, 20, 25, 30, 35, 40, 45, 50, 55, 60, 65, 70, 75, 80, 85, 90, 95 or 100 ng of the nucleic acid molecule of the vaccine. In some embodiments, the pharmaceutical compositions can comprise at least 1, 5, 10, 15, 20, 25, 30, 35, 40, 45, 50, 55, 60, 65, 70, 75, 80, 85, 90, 95, 100, 105, 110, 115, 120, 125, 130, 135, 140, 145, 150, 155, 160, 165, 170, 175, 180, 185, 190, 195, 200, 205, 210, 215, 220, 225, 230, 235, 240, 245, 250, 255, 260, 265, 270, 275, 280, 285, 290, 295, 300, 305, 310, 315, 320, 325, 330, 335, 340, 345, 350, 355, 360, 365, 370, 375, 380, 385, 390, 395, 400, 405, 410, 415, 420, 425, 430, 435, 440, 445, 450, 455, 460, 465, 470, 475, 480, 485, 490, 495, 500, 505, 610, 615, 620, 625, 630, 635, 640, 645, 650, 655, 660, 665, 670, 675, 680, 685, 690, 695, 700, 705, 710, 715, 720, 725, 730, 735, 740, 745, 750, 755, 760, 765, 770, 775, 780, 785, 790, 795, 800, 805, 810, 815, 820, 825, 830, 835, 840, 845, 850, 855, 860, 865, 870, 875, 880, 885, 890, 895. 900, 905, 910, 915, 920, 925, 930, 935, 940, 945, 950, 955, 960, 965, 970, 975, 980, 985, 990, 995 or 1000 micrograms of the nucleic acid molecule of the vaccine. In some embodiments, the pharmaceutical composition can comprise at least 1.5, 2, 2.5, 3, 3.5, 4, 4.5, 5, 5.5, 6, 6.5, 7, 7.5, 8, 8.5, 9, 9.5 or 10 mg or more of the nucleic acid molecule of the vaccine.

In other embodiments, the pharmaceutical composition can comprise up to and including 15, 20, 25, 30, 35, 40, 45, 50, 55, 60, 65, 70, 75, 80, 85, 90, 95 or 100 ng of the nucleic acid molecule of the vaccine. In some embodiments, the pharmaceutical composition can comprise up to and including 1, 5, 10, 15, 20, 25, 30, 35, 40, 45, 50, 55, 60, 65, 70, 75, 80, 85, 90, 95, 100, 105, 110, 115, 120, 125, 130, 135, 140, 145, 150, 155, 160, 165, 170, 175, 180, 185, 190, 195, 200, 205, 210, 215, 220, 225, 230, 235, 240, 245, 250, 255, 260, 265, 270, 275, 280, 285, 290, 295, 300, 305, 310, 315, 320, 325, 330, 335, 340, 345, 350, 355, 360, 365, 370, 375, 380, 385, 390, 395, 400, 405, 410, 415, 420, 425, 430, 435, 440, 445, 450, 455, 460, 465, 470, 475, 480, 485, 490, 495, 500, 605, 610, 615, 620, 625, 630, 635, 640, 645, 650, 655, 660, 665, 670, 675, 680, 685, 690, 695, 700, 705, 710, 715, 720, 725, 730, 735, 740, 745, 750, 755, 760, 765, 770, 775, 780, 785, 790, 795, 800, 805, 810, 815, 820, 825, 830, 835, 840, 845, 850, 855, 860, 865, 870, 875, 880, 885, 890, 895. 900, 905, 910, 915, 920, 925, 930, 935, 940, 945, 950, 955, 960, 965, 970, 975, 980, 985, 990, 995, or 1000 micrograms of the nucleic acid molecule of the vaccine. In some embodiments, the pharmaceutical composition can comprise up to and including 1.5, 2, 2.5, 3, 3.5, 4, 4.5, 5, 5.5, 6, 6.5, 7, 7.5, 8, 8.5, 9, 9.5 or 10 mg of the nucleic acid molecule of the vaccine.

The pharmaceutical composition can further comprise other agents for formulation purposes according to the mode of administration to be used. In cases where pharmaceutical compositions are injectable pharmaceutical compositions, they are sterile, pyrogen free and particulate free. An isotonic formulation is preferably used. Generally, additives for isotonicity can include sodium chloride, dextrose, mannitol, sorbitol and lactose. In some cases, isotonic solutions such as phosphate buffered saline are preferred. Stabilizers include gelatin and albumin. In some embodiments, a vasoconstriction agent is added to the formulation.

The pharmaceutical composition can further comprise a pharmaceutically acceptable excipient as provided above. For example, the pharmaceutically acceptable excipient can comprise the functional molecules, vehicles, adjuvants, carriers, diluents, or transfection facilitating agents, as provided above.

Methods of Vaccination

Provided herein are methods for treating and/or preventing mesothelin-expressing cancer, such as but not limited to ovarian cancer, using the pharmaceutical formulations described above. Also described herein are methods of using the pharmaceutical formulations described above in the treatment and/or prevention of mesothelin-expressing cancer, such as but not limited to ovarian cancer, in a subject. Also described herein are methods of vaccinating a subject. Also described herein are methods of administering the pharmaceutical formulations described herein to a subject in need thereof. The methods described herein collectively referred to as methods of treatment using the pharmaceutical formulations described herein can comprise administering one or more vaccine as described herein to a subject in need thereof to induce a therapeutic and/or prophylactic immune response. The vaccine can be administered to a subject to modulate the activity of the subject's immune system and enhance the immune response. The administration of the vaccine can be the transfection of the cancer antigens as disclosed herein as a nucleic acid molecule that is expressed in the cell and delivered to the surface of the cell, whereupon the immune system recognizes and induces a cellular, humoral, or cellular and humoral response. The administration of the vaccine can be used to induce or elicit an immune response in subjects against mesothelin by administering to the subject the vaccine as discussed herein.

The vaccine can be administered to a subject to modulate the activity of the subject's immune system, thereby enhancing the immune response. In some embodiments, the subject is a mammal. Upon administration of the vaccine to the mammal, and thereby introducing the vector into the cells of the mammal, the transfected cells will express and secrete one or more of the cancer antigens as disclosed herein. These secreted proteins, or synthetic antigens, will be recognized as foreign by the immune system, which will mount an immune response that can include: antibodies made against the one or more cancer antigens, and T-cell response specifically against the one or more cancer antigens. In some examples, a mammal vaccinated with the vaccines discussed herein will have a primed immune system and when challenged with the one or more cancer antigens as disclosed herein, the primed immune system will allow for rapid clearing of subsequent cancer antigens as disclosed herein, whether through the humoral, cellular, or both cellular and humoral immune responses.

Methods of administering the DNA of a vaccine are described in U.S. Pat. Nos. 4,945,050 and 5,036,006, both of which are incorporated herein in their entirety by reference.

The vaccine can be administered to a mammal to elicit an immune response in a mammal. The mammal can be human, non-human primate, cow, pig, sheep, goat, antelope, bison, water buffalo, bovids, deer, hedgehogs, elephants, llama, alpaca, mice, rats, and preferably human, cow, or pig. The vaccine can likewise be administered to a non-mammal subject, for example, a chicken, to elicit an immune response.

The vaccine dose can be between 1 microgram and 10 mg active component per kilogram (kg) body weight over time (component/kg body weight/time), and can be 20 micrograms to 10 mg component/kg body weight/time. The vaccine can be administered every 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, or 31 days. The number of vaccine doses for effective treatment can be 1, 2, 3, 4, 5, 6, 7, 8, 9, 10, or more doses.

Method of Generating an Immune Response with the Vaccine

The vaccine can be used to generate an immune response in a mammal or non-mammal subject, including therapeutic or prophylactic immune response. The immune response can generate antibodies and/or killer T cells which are directed to the one or more cancer antigens as disclosed herein. Such antibodies and T cells can be isolated.

Some embodiments provide methods of generating immune responses against one or more of the cancer antigens as disclosed herein, which embodiments comprise administering the vaccine to a subject. Some embodiments provide methods of prophylactically vaccinating a subject against a cancer or tumor expressing one or more of the mesothelin antigens as described above, which embodiments comprise administering the vaccine. Some embodiments provide methods of therapeutically vaccinating a subject that has been suffering from the ovarian cancer or tumor expressing mesothelin, which embodiments comprise administering the vaccine. Diagnosis of the ovarian cancer or tumor expressing the one or more mesothelin antigens as disclosed herein prior to administration of the vaccine can be done routinely.

Method of Cancer Treatment with the Vaccine

The vaccine can be used to generate or elicit an immune response in a mammal that is reactive or directed to mesothelin-expressing cancer, such as but not limited to ovarian cancer, more particularly epithelial ovarian cancer, most particularly serous ovarian cancer. The elicited immune response can prevent ovarian cancer or tumor growth.

The elicited immune response can prevent and/or reduce metastasis of cancerous or tumor cells in a subject with ovarian cancer. Accordingly, the vaccine can be used in a method that treats and/or prevents cancer or tumors in the mammal or subject with cancer that is administered the vaccine.

In some embodiments, the administered vaccine can mediate clearance or prevent growth of tumor cells by inducing (1) humoral immunity via B cell responses to generate antibodies that block monocyte chemoattractant protein-1 (MCP-1) production, thereby retarding myeloid derived suppressor cells (MDSCs) and suppressing tumor growth; (2) increase cytotoxic T lymphocyte such as CD8+ (CTL) to attack and kill tumor cells; (3) increase T helper cell responses; (4) and increase inflammatory responses via IFN-γ and TFN-α or preferably all of the aforementioned. The vaccine can increase tumor free survival by 30%, 31%, 32%, 33%, 34%, 35%, 36%, 37%, 38%, 39%, 40%, 41%, 42%, 43%, 44%, and 45%. The vaccine can reduce tumor mass by 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, and 60% after immunization. The vaccine can prevent and block increases in monocyte chemoattractant protein 1 (MCP-1), a cytokine secreted by myeloid derived suppressor cells. The vaccine can increase tumor survival by 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, and 60%.

In some embodiments, the immune response can generate a humoral immune response and/or an antigen-specific cytotoxic T lymphocyte (CTL) response that does not cause damage to or inflammation of various tissues or systems (e.g., brain or neurological system, etc.) in the subject administered the vaccine.

In some embodiments, the vaccine can be administered to the periphery (as described in more detail below) to establish an antigen-specific immune response targeting the cancerous or tumor cells or tissue to clear or eliminate the cancer or tumor expressing the one or more cancer antigens without damaging or causing illness or death in the subject administered the vaccine.

The administered vaccine can increase a cellular immune response in the subject by about 50-fold to about 6000-fold, about 50-fold to about 5500-fold, about 50-fold to about 5000-fold, about 50-fold to about 4500-fold, about 100-fold to about 6000-fold, about 150-fold to about 6000-fold, about 200-fold to about 6000-fold, about 250-fold to about 6000-fold, or about 300-fold to about 6000-fold. In some embodiments, the administered vaccine can increase the cellular immune response in the subject by about 50-fold, 100-fold, 150-fold, 200-fold, 250-fold, 300-fold, 350-fold, 400-fold, 450-fold, 500-fold, 550-fold, 600-fold, 650-fold, 700-fold, 750-fold, 800-fold, 850-fold, 900-fold, 950-fold, 1000-fold, 1100-fold, 1200-fold, 1300-fold, 1400-fold, 1500-fold, 1600-fold, 1700-fold, 1800-fold, 1900-fold, 2000-fold, 2100-fold, 2200-fold, 2300-fold, 2400-fold, 2500-fold, 2600-fold, 2700-fold, 2800-fold, 2900-fold, 3000-fold, 3100-fold, 3200-fold, 3300-fold, 3400-fold, 3500-fold, 3600-fold, 3700-fold, 3800-fold, 3900-fold, 4000-fold, 4100-fold, 4200-fold, 4300-fold, 4400-fold, 4500-fold, 4600-fold, 4700-fold, 4800-fold, 4900-fold, 5000-fold, 5100-fold, 5200-fold, 5300-fold, 5400-fold, 5500-fold, 5600-fold, 5700-fold, 5800-fold, 5900-fold, or 6000-fold as compared to the cellular immune response in the subject not administered the vaccine.

The administered vaccine can increase interferon gamma (IFN-γ) levels in the subject by about 50-fold to about 6000-fold, about 50-fold to about 5500-fold, about 50-fold to about 5000-fold, about 50-fold to about 4500-fold, about 100-fold to about 6000-fold, about 150-fold to about 6000-fold, about 200-fold to about 6000-fold, about 250-fold to about 6000-fold, or about 300-fold to about 6000-fold. In some embodiments, the administered vaccine can increase IFN-γ levels in the subject by about 50-fold, 100-fold, 150-fold, 200-fold, 250-fold, 300-fold, 350-fold, 400-fold, 450-fold, 500-fold, 550-fold, 600-fold, 650-fold, 700-fold, 750-fold, 800-fold, 850-fold, 900-fold, 950-fold, 1000-fold, 1100-fold, 1200-fold, 1300-fold, 1400-fold, 1500-fold, 1600-fold, 1700-fold, 1800-fold, 1900-fold, 2000-fold, 2100-fold, 2200-fold, 2300-fold, 2400-fold, 2500-fold, 2600-fold, 2700-fold, 2800-fold, 2900-fold, 3000-fold, 3100-fold, 3200-fold, 3300-fold, 3400-fold, 3500-fold, 3600-fold, 3700-fold, 3800-fold, 3900-fold, 4000-fold, 4100-fold, 4200-fold, 4300-fold, 4400-fold, 4500-fold, 4600-fold, 4700-fold, 4800-fold, 4900-fold, 5000-fold, 5100-fold, 5200-fold, 5300-fold, 5400-fold, 5500-fold, 5600-fold, 5700-fold, 5800-fold, 5900-fold, or 6000-fold as compared to IFN-γ levels in the subject not administered the vaccine.

The vaccine dose can be between 1 microgram and 10 mg active component per kilogram (kg) body weight over time (component/kg body weight/time), and can be 20 micrograms to 10 mg component/kg body weight/time. The vaccine can be administered every 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, or 31 days. The number of vaccine doses for effective treatment can be 1, 2, 3, 4, 5, 6, 7, 8, 9, 10, or more doses.

Routes of Administration

The vaccine or pharmaceutical composition can be administered by different routes including orally, parenterally, sublingually, transdermally, rectally, transmucosally, topically, via inhalation, via buccal administration, intrapleurally, intravenously, intraarterially, intraperitoneally, subcutaneously, intramuscularly, intranasal intrathecally, and/or intraarticularly, or combinations thereof. For veterinary use, the composition can be administered as a suitably acceptable formulation in accordance with normal veterinary practice. The veterinarian can readily determine the dosing regimen and route of administration that is most appropriate for a particular animal. The vaccine can be administered by traditional syringes, needleless injection devices, "microprojectile bombardment gene guns", or other physical methods such as electroporation ("EP"), "hydrodynamic method", or ultrasound.

The vector of the vaccine can be administered to the mammal by several well-known technologies including DNA injection (also referred to as DNA vaccination) with and without in vivo electroporation, liposome mediated transfection, nanoparticle facilitated transfection, and use recombinant vectors such as recombinant adenovirus, recombinant adenovirus associated virus, and recombinant vaccinia. The one or more cancer antigens of the vaccine can be administered via DNA injection along with in vivo electroporation.

Electroporation

The vaccine or pharmaceutical composition can be administered by electroporation. Administration of the vaccine via electroporation can be accomplished using electroporation devices that can be configured to deliver to a desired tissue of a mammal a pulse of energy effective to cause reversible pores to form in cell membranes, and preferably the pulse of energy is a constant current similar to a preset current input by a user. The electroporation device can comprise an electroporation component and an electrode assembly or handle assembly. The electroporation component can include and incorporate one or more of the various elements of the electroporation devices, including: controller, current waveform generator, impedance tester, waveform logger, input element, status reporting element, communication port, memory component, power source, and power switch. The electroporation can be accomplished using an in vivo electroporation device, for example CELLECTRA® EP system (Inovio Pharmaceuticals, Inc., Blue Bell, Pa.) or Elgen electroporator (Inovio Pharmaceuticals, Inc.) to facilitate transfection of cells by the plasmid.

Examples of electroporation devices and electroporation methods that can facilitate administration of the DNA vaccines of the present invention include those described in U.S. Pat. No. 7,245,963 by Draghia-Akli, et al., U.S. Patent Pub. 2005/0052630 submitted by Smith, et al., the contents of which are hereby incorporated by reference in their entirety. Other electroporation devices and electroporation methods that can be used for facilitating administration of the DNA vaccines include those provided in co-pending and co-owned U.S. patent application Ser. No. 11/874,072, filed Oct. 17, 2007, which claims the benefit under 35 USC 119(e) to U.S. Provisional Application Ser. No. 60/852,149, filed Oct. 17, 2006, and 60/978,982, filed Oct. 10, 2007, all of which are hereby incorporated in their entirety.

U.S. Pat. No. 7,245,963 by Draghia-Akli, et al. describes modular electrode systems and their use for facilitating the introduction of a biomolecule into cells of a selected tissue in a body or plant. The modular electrode systems can comprise a plurality of needle electrodes; a hypodermic needle; an electrical connector that provides a conductive link from a programmable constant-current pulse controller to the plurality of needle electrodes; and a power source. An operator can grasp the plurality of needle electrodes that are mounted on a support structure and firmly insert them into the selected tissue in a body or plant. The biomolecules are then administering via the hypodermic needle into the selected tissue. The programmable constant-current pulse controller is activated and constant-current electrical pulse is applied to the plurality of needle electrodes. The applied constant-current electrical pulse facilitates the introduction of the biomolecule into the cell between the plurality of electrodes. The entire content of U.S. Pat. No. 7,245,963 is hereby incorporated by reference in its entirety.

U. S. Patent Pub. 2005/0052630 submitted by Smith, et al. describes an electroporation device which can be used to effectively facilitate the introduction of a biomolecule into cells of a selected tissue in a body or plant. The electroporation device comprises an electro-kinetic device ("EKD device") whose operation is specified by software or firmware. The EKD device produces a series of programmable constant-current pulse patterns between electrodes in an array based on user control and input of the pulse parameters, and allows the storage and acquisition of current waveform data. The electroporation device also comprises a replaceable electrode disk having an array of needle electrodes, a central injection channel for an injection needle, and a removable guide disk. The entire content of U.S. Patent Pub. 2005/0052630 is hereby fully incorporated by reference.

The electrode arrays and methods described in U.S. Pat. No. 7,245,963 and U.S. Patent Pub. 2005/0052630 can be adapted for deep penetration into not only tissues such as muscle, but also other tissues or organs. Because of the configuration of the electrode array, the injection needle is also inserted completely into the target organ, and the injection is administered perpendicular to the target issue, in the area that is pre-delineated by the electrodes. The electrodes described in U.S. Pat. No. 7,245,963 and U.S. Patent Pub. 2005/005263 are preferably 20 mm long and 21 gauge.

Additionally, contemplated in some embodiments that incorporate electroporation devices and uses thereof, there are electroporation devices that are those described in the following patents: U.S. Pat. No. 5,273,525 issued Dec. 28, 1993, U.S. Pat. No. 6,110,161 issued Aug. 29, 2000, U.S. Pat. No. 6,261,281 issued Jul. 17, 2001, and U.S. Pat. No. 6,958,060 issued Oct. 25, 2005, and U.S. Pat. No. 6,939,862 issued Sep. 6, 2005. Furthermore, patents covering subject matter provided in U.S. Pat. No. 6,697,669 issued Feb. 24, 2004, which concerns administration of DNA using any of a variety of devices, and U.S. Pat. No. 7,328,064 issued Feb. 5, 2008, drawn to method of injecting DNA are contemplated herein. The above-patents are incorporated by reference in their entirety.

Methods of Preparing the Vaccine

Provided herein are methods for preparing the DNA plasmids discussed herein. The DNA plasmids, after the final subcloning step into the mammalian expression plasmid, can be used to inoculate a cell culture in a large scale fermentation tank, using known methods in the art.

The DNA plasmids for use with the electroporation devices of the present invention can be formulated or manufactured using a combination of known devices and techniques, but preferably they are manufactured using an optimized plasmid manufacturing technique that is described in a US published application no. 20090004716, which was filed on May 23, 2007. In some examples, the DNA plasmids used in these studies can be formulated at concentrations greater than or equal to 10 mg/mL. The manufacturing techniques also include or incorporate various devices and protocols that are commonly known to those of ordinary skill in the art, in addition to those described in U.S. Ser. No. 60/939,792, including those described in a licensed patent, U.S. Pat. No. 7,238,522, which issued on Jul. 3, 2007. The above-referenced application and patent, U.S. Ser. No. 60/939,792 and U.S. Pat. No. 7,238,522, respectively, are hereby incorporated in their entirety.

The present invention has multiple aspects, illustrated by the following non-limiting examples.

EXAMPLES

The present invention is further illustrated in the following Examples. It should be understood that these Examples, while indicating preferred embodiments of the invention, are given by way of illustration only. From the above discussion and these Examples, one skilled in the art can ascertain the essential characteristics of this invention, and without departing from the spirit and scope thereof, can make various changes and modifications of the invention to adapt it to various usages and conditions. Thus, various modifications of the invention in addition to those shown and described herein will be apparent to those skilled in the art from the foregoing description. Such modifications are also intended to fall within the scope of the appended claims.

Example 1: Generation of Consensus Mesothelin Sequence

Three mesothelin variants have been reported in GenBank. Variants 1 and 2 are 98% identical at the nucleotide level and variant 3 is a partial sequence with an alternatively spliced C-terminus disrupting the GPI anchor region. All three transcript variants have been reported to be expressed by human cancer cells. Based on sequence analysis, a vaccine targeting variant 1 would also target a majority of the sequence in variants 2 and 3. In addition, variant 1 is the major transcript expressed in ovarian tumors. Therefore, variant 1 was selected as the vaccine target.

In order to generate a human consensus mesothelin human, 14 mesothelin sequences were collected from GenBank (www.ncbi.nlm.nih.gov/genbank/). The GenBank accession numbers for the selected Mesothelin sequences are: NP_005814.2, BAA08419.1, AAH09272.1, AAV87530.1, AAH03512.1, XP_008959182.1, AAC50348.1, XP_009428309.1, XP_007978969.1, XP_011822299.1, XP_011817841.1, XP_011822298.1, XP_009193880.1, and XP_011817843.1.

A consensus sequence was generated using the DNASTAR® Lasergene software package (version 13.0.0.357). The mesothelin sequences from GenBank were imported into MegAlign and aligned using the ClustalW multiple sequence alignment program. The resulting mesothelin consensus sequence (SEQ ID NO: 1) shares 95.8% homology with the native human mesothelin.

Example 2: Introduction of Mutations to Abolish Function of Mesothelin

In order to abolish the potential biological function of the resulting consensus mesothelin protein, one mutation was introduced to abolish MUC16/CA125 binding. Additionally, two mutations were introduced to disrupt GPI-attachment. The rationale for the introduction of these mutations is described below.

MUC16/CA125 Binding Mutation

Truncated mutagenesis was used to identify a binding site on mesothelin for MUC16/CA125 (FIG. 1). As illustrated in FIG. 1, the mesothelin precursor (71-kDa) is cleaved into two products, the 30-kDa megakaryocyte potentiating factor (MPF; residues Ser34-Arg286) and the 41-kDa GPI-anchored membrane-bound mature mesothelin (light gray) starting from Glu296. The proteolytic cleavage region (hatched gray) contains a furin cleavage site at Arg295, and other protease cleavage sites including a trypsin cleavage site at Arg286. The four predicted N-linked glycans (black lollipops; Asn57, Asn388, Asn488, and Asn515) on mesothelin are indicated. Truncated mutants (Regions I, II, III, IAB, IBC, IA, IB, and IC) were generated as rabbit Fc fusion proteins to sequentially narrow down the CA125-binding domain of mesothelin.

Figure 5:
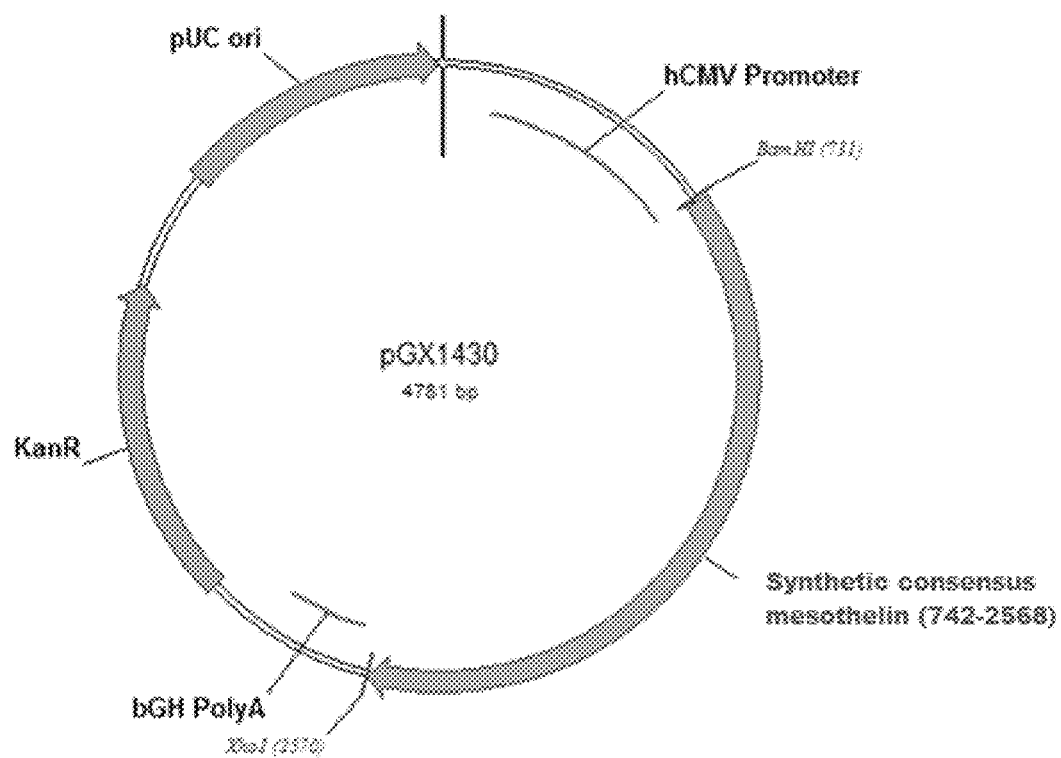
FIG. 5 is a diagrammatic representation of plasmid pGX1438.

As shown in FIG. 5 of Kaneko et al., *J Biol Chem*, 2009 Feb. 6; 284(6):3739-49, substitution of the tyrosine at position 318 with an alanine (Y318A) completely disrupted the interaction with CA125. Alanine mutation at Glu324 (E324A; KD 42.4 nM) and Trp321 (W321A; KD 19.5 nM) reduced the binding of mesothelin to CA125. The alanine mutation at His354 (H354A) did not change the mesothelin-CA125 interaction (KD 2.71 nM).

Figure 4:
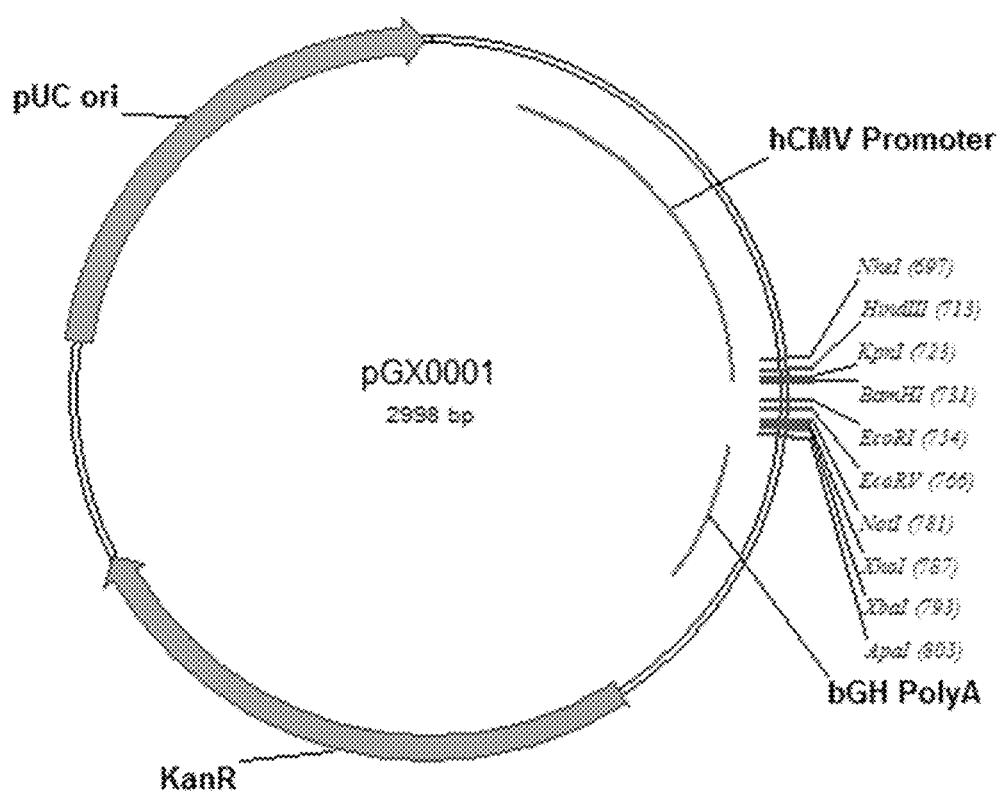
FIG. 4 is a diagrammatic representation of the modified pVAX1 backbone (pGX0001).

And as shown in FIG. 4 of Kaneko et al., *J Biol Chem*, 2009 Feb. 6; 284(6):3739-49, Western blots of alanine mutants within Region IAB (296-359) show differential binding. Alanine mutations at Tyr318 (Y318A) and Glu324 (E324A) abolished the binding of mesothelin to CA125. Alanine mutation at Trp321 (W321A) partially reduced the binding of mesothelin to CA125. The alanine mutation at His354 did not change the mesothelin-CA125 interaction.

Figure 6:
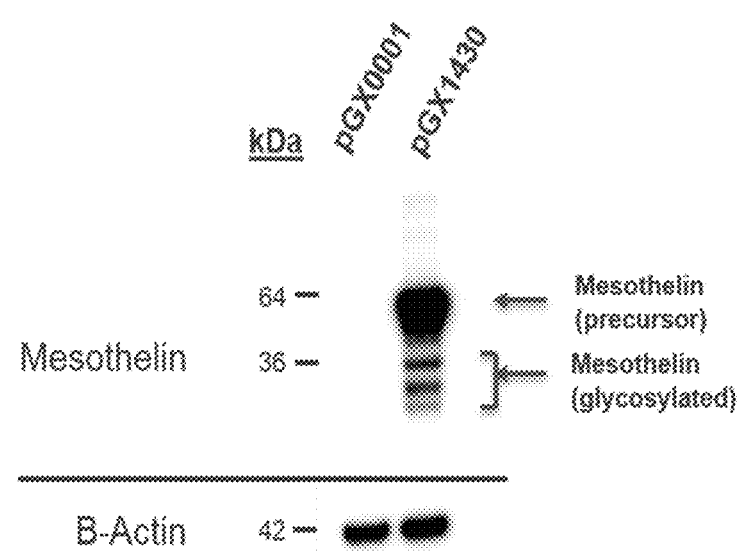
FIG. 6 shows a Western blot of synthetic consensus mesothelin antigen expression in human rhabdomyosarcoma cells.

Finally, as shown in FIG. 6 of Kaneko et al., *J Biol Chem*, 2009 Feb. 6; 284(6):3739-49, fluorescence intensity (geometrical mean) was used to quantitatively measure the CA125 binding. The binding of the full-length mature form of mesothelin (FULL) to CA125 was determined as 100% of binding. Region I (296-390), Region IAB (296-359), and the H354A mutant of IAB bound to CA125 significantly stronger than any other fragments or mutants listed (*, p_0.05). The Y318A mutation greatly reduced binding as compared to the full-length mature form of mesothelin. Based on these findings, the Y318A mutation was introduced into the final synthetic consensus mesothelin sequence.

GPI-Attachment Site

Figure 2:
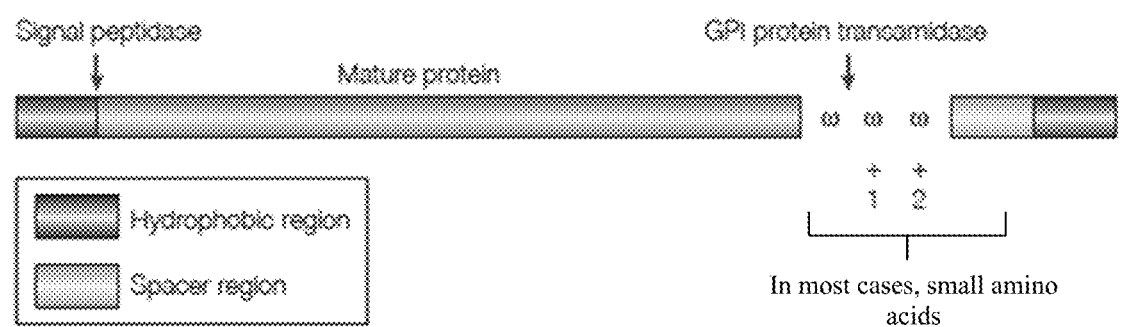
FIG. 2 is a schematic of the structure of the GPI-anchored-mesothelin protein precursor.

The GPI-anchoring signal consists of a hydrophobic region separated from the GPI-attachment site (w-site) by a hydrophilic spacer region (FIG. 2). The attachment site is the first of three contiguous amino acids that have short side chains. It must be followed by a short spacer sequence, which is usually unstructured, and then by a carboxy-terminal, hydrophobic signaling sequence. Mayor, S. & Riezman, H. *Nature reviews. Molecular cell biology* 5 (2004). The ω-site in mesothelin was mutated from serine to threonine. The ω+2 in mesothelin was mutated from threonine to valine.

As shown in Table 1, the synthetic consensus mesothelin protein sequence shares 95.2% identity with human native mesothelin.

TABLE 1

| | Percent Identity | | | |
|---|---|---|---|---|
| Divergence | | 1 | 2 | |
| | 1 | | 95.2 | 1 |
| | 2 | 4.9 | | 2 |
| | | 1 | 2 | |

1 = Consensus mesothelin
2 = Mesothelin NP_085814

Example 3: Characterization of Synthetic Consensus Mesothelin Construct

Once the synthetic consensus mesothelin DNA sequence was obtained, in order to have a higher level of expression, an upstream Kozak sequence and IgE leader sequence were added to the N-terminus. Yang, J. S. et al. *The Journal of infectious diseases* 184, 809-816 (2001). Furthermore, the codon usage of the gene was adapted to the codon bias of *Homo sapiens* genes. Andre, S. et al. *Journal of virology* 72, 1497-1503 (1998); Deml, L. et al. *Journal of virology* 75, 10991-11001 (2001). RNA optimization was also performed such that regions of very high (>80%) or very low (<30%) GC content and the cis-acting sequence motifs such as internal TATA boxes, chi-sites and ribosomal entry sites were avoided. Muthumani, K. et al. Virology 314, 134-146 (2003); Muthumani, K. et al. *Virology* 314, 134-146 (2003).

Figure 3:
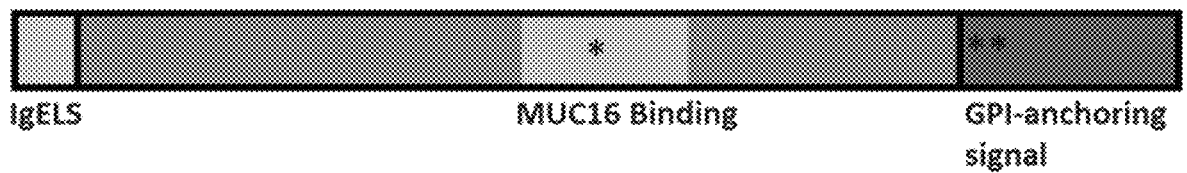
FIG. 3 shows a schematic of the synthetic consensus mesothelin.

A schematic representation of the synthetic consensus mesothelin construct is shown in FIG. 3. The asterisk (*) denotes mutations to abolish MUC16 binding and GPI attachment. The nucleotide sequence (SEQ ID NO. 1) and amino acid (SEQ ID NO. 2) for synthetic consensus mesothelin are presented in Table 16 and Table 17, respectively. An annotation of the elements of SEQ ID NO: 2 and the corresponding amino acid positions are provided in Table 2.

TABLE 2

| Description | Amino acid position |
|---|---|
| IgE leader sequence | 1-18 |
| Mesothelin coding sequence | 19-607 |
| Mutation to abolish MUC16/CA125 binding | Y303A |
| Mutations to disrupt GPI-attachment | S583T |
| | T585V |

In order to better understand possible protein structural effects of the synthetic consensus design process, a comparative model of the molecular precursor of MPF and mesothelin was generated. Multiple secondary structure elements were used to align and generate the model. A predicted glycosylation site is correctly oriented on the surface of the model. The mesothelin portion of the model was extrapolated from work done by Sathyanarayana et al. and was modeled as a series of ARM repeats. Sathyanarayana, B. K., Hahn, Y. et al. *BMC structural biology* 9, 1 (2009) The Sathyanarayana reference did not appear to address the location of a disulfide bond. This feature is addressed in the improved model and is correctly oriented locally. In addition, the potential N-linked glycosites are surface-accessible.

The characteristics of the synthetic consensus mesothelin are summarized in Table 3.

TABLE 3

| Characteristics | Synthetic Consensus Mesothelin |
|---|---|
| Identity to native human mesothelin | 95.2% |
| Identity to native rhesus mesothelin | 90.3% |
| Identity to native mouse mesothelin | 58.1% |
| Number of amino acid mutations (vs native human) | 28 |
| Number of inserted mutations (not consensus derived) | 3 |
| Molecular weight | 609 aa (67 KDa) |
| Length of coding sequence (bp) | 1827 |

Example 4: Plasmid Construction and Structure

The vector backbone is pGX0001, a 2998 bp modified pVAX1 expression vector under the control of the human cytomegalovirus immediate-early promoter (hCMV promoter). The original pVAX1 was obtained from Thermo Fisher Scientific. The pGX0001 backbone includes the kanamycin resistance gene (KanR) and plasmid origin of replication (pUC ori) for production purpose. Those elements are not functional in eukaryotic cells. The map and description of the modified expression vector pVAX1 (pGX0001) are shown in FIG. 4.

Modifications were introduced into pVAX1 to create pGX0001. These modifications are listed in Table 4, and no issues have been detected regarding plasmid amplification and antigen transcription and translation. No further changes in the sequence of pGX0001 have been observed to date using pGX0001 as the backbone. Base pairs 2, 3 and 4 are changed from ACT to CTG in backbone, upstream of CMV promoter.

TABLE 4

| Modification | Base Pair | Description |
|---|---|---|
| C > G | 241 | in CMV promoter |
| C > T | 1158 | backbone, downstream of the bovine growth hormone polyadenylation signal (bGH polyA) |
| A > — | 2092 | backbone, downstream of the Kanamycin resistance gene |
| C > T | 2493 | in pUC origin of replication (pUC ori) |
| G > C | 2969 | in very end of pUC Ori upstream of RNASeH site |

The synthesized synthetic consensus mesothelin was digested with BamHI and XhoI, and cloned into pGX0001 with the expression cassette placed under the transcription control of the cytomegalovirus immediate-early promoter. The resulting plasmid was designated pGX1430. Full length sequencing was performed and then analyzed and confirmed by two analysts to be correct. A schematic diagram of pGX1430 is presented FIG. 5.

Example 5: In Vitro Antigen Expression

Expression of the antigen protein by pGX1430 was confirmed by western blotting. Human rhabdomyosarcoma (RD) cells (ATCC, CCL-136) maintained in DMEM medium with 10% FBS (ThermoFisher) were transfected with pGX1430 or pGX0001 (6 µg/10 cm2 dish) using Turbofectin 8 (Origene). Forty-eight hours after transfection, the cells were lysed using RIPA cell lysis buffer (ThermoFisher) and cell lysate was collected. Following a BCA assay (ThermoFisher) to determine total protein concentration, 15 µg of cell lysate was electrophoresed on a 4-12% SDS-PAGE gel (ThermoFisher) and detection was performed using a commercially available anti-mesothelin antibody (Cell Signaling Technology clone D4X7M) then visualized with horseradish peroxidase (HRP)-conjugated anti-rabbit IgG (Santa Cruz Biotech #sc-2004) using an ECL western blot analysis system (GE Healthcare). As a loading control, blots were re-probed for actin expression using an anti-β-actin monoclonal antibody (Santa Cruz Biotech, clone, C4).

Human mesothelin precursor is 70 kDa with cleaved glycosylated forms at 46-48 kDa whereas synthetic consensus mesothelin prescursor is 64.28 kDa with cleaved glycosylated forms at 35-37 kDa. As shown in FIG. 6, a protein band of the expected molecular weight was detected for pGX1430 (64.28 kD). No protein bands were detected in the pGX0001 lane. Anti-β-actin bands were detected of similar intensities indicating equal amounts of protein were loaded in each lane.

Example 6: Immunogenicity of the Synthetic Consensus Mesothelin Vaccine Constructs Animals and Immunizations Female, 8-week-old CB6F1 mice were purchased from Jackson Laboratories. All animals were housed in a temperature-controlled, light-cycled facility at BTS Research (San Diego, Calif.). Animal care was carried out according to the guidelines of the National Institutes of Health and the Animal Care and Use Proposal (ACUP) (BTS ACUP #15-091). Mice were divided into five groups as detailed in Table 5.

TABLE 5

| Group | n | Construct | Construct Dose (µg) | Injection volume (µl) |
|---|---|---|---|---|
| 1 | 4 | pGX0001 | 30 | 30 |
| 2 | 8 | pGX1430 | 10 | 30 |
| 3 | 8 | pGX1430 | 20 | 30 |
| 4 | 8 | pGX1430 | 30 | 30 |
| 5 | 8 | pGX1430 | 50 | 30 |

The mice in the immunized groups were vaccinated with the doses indicated of pGX0001 or pGX1430 according to SOP R20-003147 CELLECTRA® 3P Mouse Treatment. Briefly, plasmids were formulated in sterile water for injection (VetOne) such that the indicated dose was delivered by intramuscular injection into the tibialis anterior muscle in a 30 µL injection volume. Each intramuscular injection was immediately followed by electroporation (EP) using the CELLECTRA® 2000 Adaptive Constant Current Electroporation Device with a 3P array (Inovio Pharmaceuticals). The device was configured to deliver two 0.1 Amp pulses of 52 ms pulse width, spaced apart by a 1 second delay. The mice received 3 immunizations, 3 weeks apart. Mice were sacrificed three weeks after the last immunization and spleens harvested for cellular immune readouts. No other tissue was collected.

Splenic Lymphocyte Isolation

Splenocytes were aseptically isolated and placed in 5 mL of R10 media (Rosewell Park Memorial Institute medium 1640 supplemented with 10% fetal bovine serum and 1% antibiotic-antimycotic). Splenocytes were isolated by mechanical disruption of the spleen using a Stomacher machine (Seward Laboratory Systems Inc.), and the resulting product was filtered using a 40-µm cell strainer (BD Falcon). The resulting product was centrifuged and the pellet was treated for 5 min with ACK lysis buffer (Lonza) for lysis of RBCs. The splenocytes were then centrifuged, washed in PBS, and then resuspended in R10 media and immediately used for further analysis.

IFNγ ELISpot

Mouse IFNγ ELISpot assay (MabTech) was performed to evaluate antigen-specific cellular responses. Ninety-six well plates pre-coated with anti-mouse IFNγ antibody were washed in PBS and blocked for 2 hours at room temperature with complete culture media (RPMI 1640 supplemented with 10% FBS and antibiotics). Splenic lymphocytes were re-suspended in R10 media (and then added in triplicates at an input cell number of 2×10$^5$ cells per well. A set of peptides was synthesized (GenScript), each containing 15 amino acid residues overlapping by 11 amino acids representing the entire synthetic consensus mesothelin protein sequence. These sets of peptides were resuspended in DMSO (Sigma) and pooled at a concentration of ~2 µg/ml peptide into two peptide pools. The peptide pool contained the peptides corresponding to the synthetic consensus mesothelin antigen protein. Concavalin A (Sigma) at 5 µg/ml was used as a positive control and complete culture medium was used as a negative control. Plates were incubated for 18 hours at 37° C., in a 5% CO$_2$ atmosphere incubator. Then, a biotinylated anti-mouse IFNγ detection antibody (MabTech) was added, and plates were incubated for 2 hours at room temperature. The plates were washed, and Streptavidin-ALP antibody (MabTech) was added and plates were incubated for 1 hour at room temperature.

Spot detection was completed according to the kit manufacturer's instructions (MabTech). The spots on the plates were counted using an automated ELISPOT reader (Cellular Technology). The average number of Spot Forming Units (SFU) was adjusted to 1×10$^6$ splenocytes for data display. Antigen specific responses by IFNγ ELISpot are reported as the number of IFNγ spot forming unit (SFU) per 1×10$^6$ splenocytes greater than the SFU in the media only control.

Figure 7A:
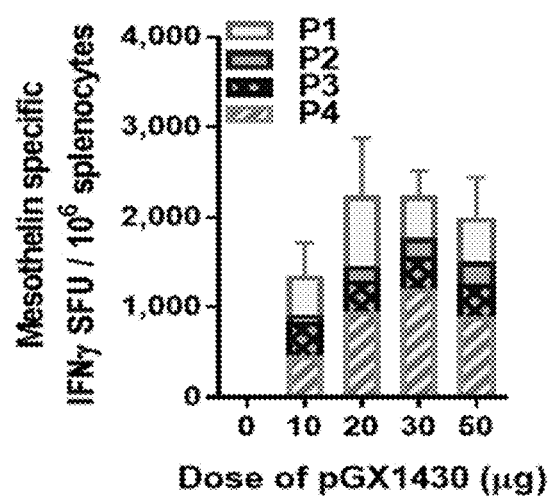
FIGS. 7A-7B illustrate the immunogenicity of synthetic consensus mesothelin using an embodiment of the disclosure.
Figure 7B:
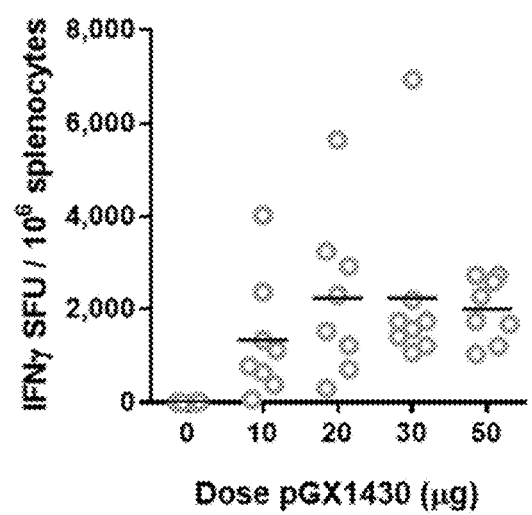

Immunogenicity of the synthetic consensus mesothelin construct was evaluated at four doses (10 µg, 20 µg, 30 µg, and 50 µg) by IFNγ ELISpot and flow cytometry (n=8/group). Mice were immunized with the empty plasmid backbone (pGX0001) as a negative control (n=4/group). Vaccination with synthetic consensus mesothelin (pGX1430) induced cellular immune responses compared to negative control vaccinated mice. The magnitude of synthetic consensus mesothelin specific IFNγ production, as determined by ELISpot, was dose-dependent at the 10 and 20 µg dose (FIG. 7A and FIG. 7B) with a similar maximal response achieved at both the 30 and 50 µg dose. Specifically, synthetic consensus mesothelin IFNγ SFU were 1345±1290, 2241±1721, 2242±1932, and 2004±674 at the 10 µg, 20 µg, 30 µg, and 50 µg, respectively. Synthetic consensus mesothelin IFNγ responses were significantly greater than naïve at the 10 µg (p=0.004), 20 µg (p=0.004), 30 µg (p=0.004), and 50 µg (p=0.004) doses of pGX1430. IFNγ responses are summarized in Table 6.

TABLE 6

| Construct | Dose | Mean SFU ± Std. Dev. | p-value |
|---|---|---|---|
| pGX0001 | 30 µg | 6 ± 7 | n/a |
| pGX1430 | 10 µg | 1345 ± 1290 | 0.004 |
| | 20 µg | 2241 ± 1721 | 0.004 |
| | 30 µg | 2242 ± 01932 | 0.004 |
| | 50 µg | 2004 ± 0674 | 0.004 |

Statistical significance assumed at $p \leq 0.013$. p-values reported are relative to naïve (pGX0001 immunized mice).

Flow Cytometry

Cellular immune responses induced by synthetic consensus mesothelin were further characterized by flow cytometry. 2×10$^6$ splenocytes from vaccinated and naïve mice were immediately stimulated following isolation with the synthetic consensus mesothelin peptides for 6 hours in the presence of Brefeldin A (BD Biosciences), Monensin (BD Biosciences), and FITC anti-mouse CD107a antibody (BD Biosciences). After stimulation with peptides, splenocytes were spun down and resuspended in 20 µL per well of mouse BD Fc Block (BD Biosciences) solution. The Fc Block is used at an initial dilution of 1:40 in PBS and incubated at 4° C. for 5 minutes.

After incubation, the remaining extracellular antibodies (in PBS) are added at 30 µL per well and allowed to incubate at 4° C. for 30 minutes. Upon addition of the extracellular stain, the final volume in each well is 50 µL, consisting of Fc Block at a final dilution of 1:100 and the extracellular antibodies at their appropriate working dilutions. Cells were then stained with viability dye (Vivid, Thermo-Fisher) and the following extracellular antibodies: APC-Cy7 anti-mouse CD3e, PerCP-Cy5.5 anti-mouse CD4, and APC anti-mouse CD8a (BD Biosciences). Intracellular cytokines were subsequently stained with the following antibodies: BV605 anti-mouse IFNγ, APC-R700 anti-mouse IL-2, and PE anti-mouse TNF-α (BD Biosciences).

Figure 8:
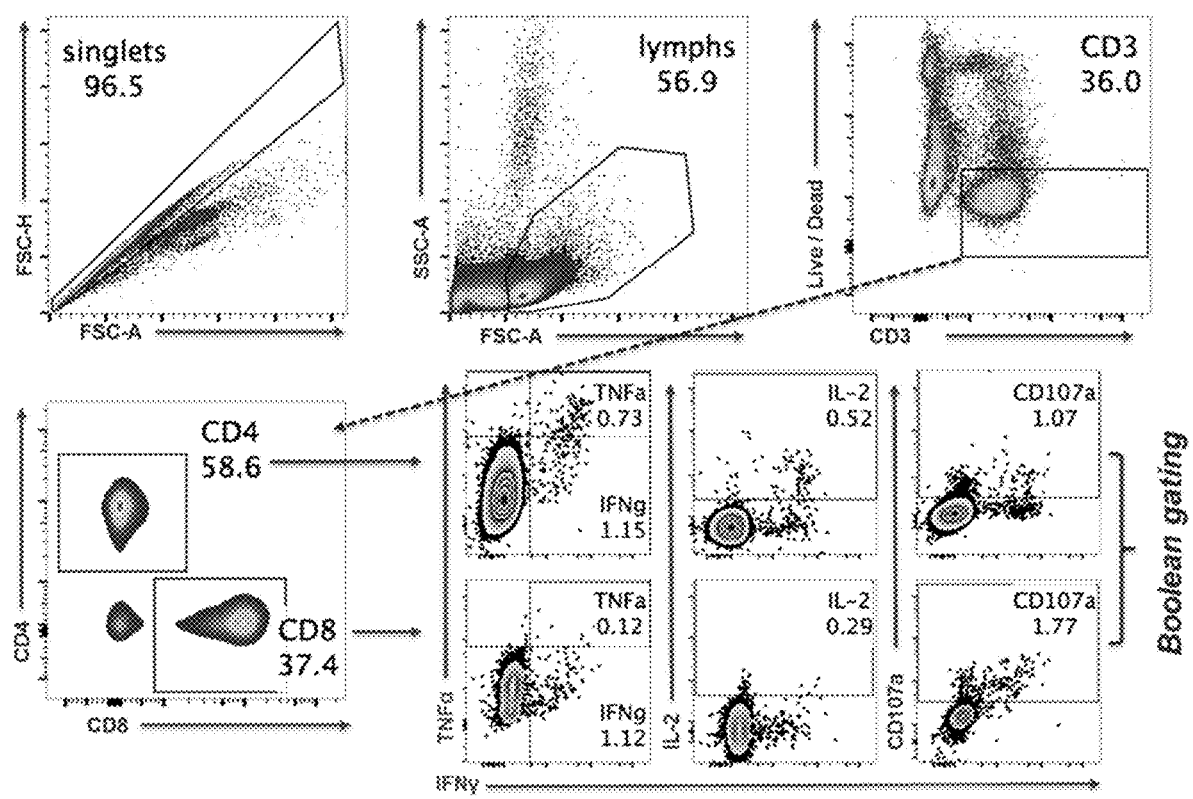
FIG. 8 illustrates the flow cytometry gating strategy using an embodiment of the disclosure.

ICS data was collected on 10-color FACS CANTO (BD Biosciences) and analysis completed using FlowJo. The flow cytometry gating strategy is shown in FIG. 8. For a cell to be called antigen specific by flow cytometry, the frequency of the reported parameter must exceed that of the media-only control. For a cell to be identified as producing antigen specific CD107a, the cell must also be identified as positive for antigen specific production of IFNγ, and/or IL-2 and/or TNFα as identified by Boolean gating.

Figure 9A:
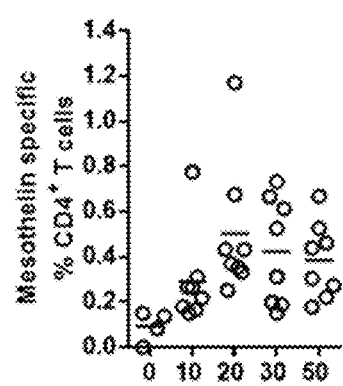
FIGS. 9A-9D illustrate cellular immune responses induced by pGX1430.
Figure 9B:
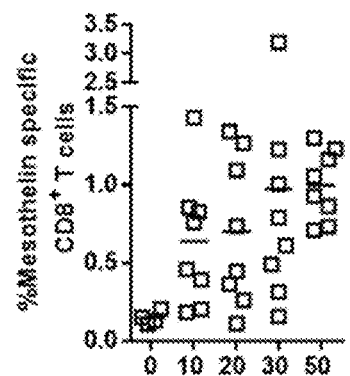
Figure 9C:
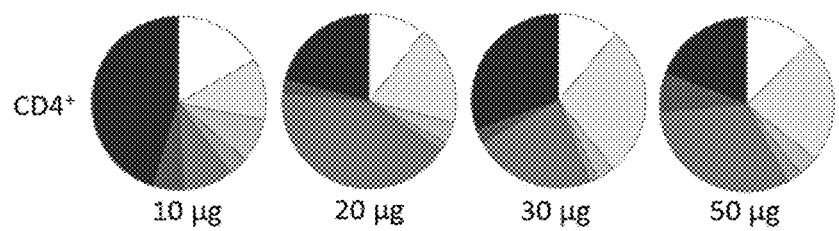

Synthetic consensus mesothelin elicited more robust responses in the CD8$^+$ T cell compartment, relative to the responses in the CD4$^+$ T cell compartment (FIGS. 9A-9D). Synthetic consensus mesothelin induced frequencies of antigen specific CD4$^+$ T cell responses that were significantly more robust than naïve (0.09%±0.07%) in the 10 µg (0.29%±0.20%) (p<0.004), 20 µg (0.50%±0.30%) (p<0.004), 30 µg (0.42%±0.24%) (p<0.004) and 50 µg (0.38%±0.17%) (p<0.004) dose groups (FIG. 9A). Synthetic consensus mesothelin specific CD4$^+$ T cell responses were dose dependent at the 10 and 20 µg doses, but not at the 30 and 50 µg doses, and consisted mainly of IFNγ-IL-2-TNFα+, IFNγ+IL-2-TNFα−, IFNγ-IL-2+TNFα+, or IFNγ+IL-2+TNFα+ producing CD4$^+$ T cells (FIG. 9C). The frequency of antigen specific CD4$^+$ T cells is further detailed in Table 7.

TABLE 7

Synthetic Consensus Mesothelin CD4+ T cells

| Construct | Dose | % CD4+ ± Std. Dev. | p-value |
|---|---|---|---|
| pGX0001 | 30 μg | 0.09 ± 0.07 | n/a |
| pGX1430 | 10 μg | 0.29 ± 0.20 | 0.004 |
|  | 20 μg | 0.50 ± 0.30 | 0.004 |
|  | 30 μg | 0.42 ± 0.24 | 0.004 |
|  | 50 μg | 0.38 ± 0.17 | 0.004 |

Statistical significance assumed at p ≤ 0.013. p-values reported are relative to naïve (pGX0001 immunized mice).

Figure 9D:
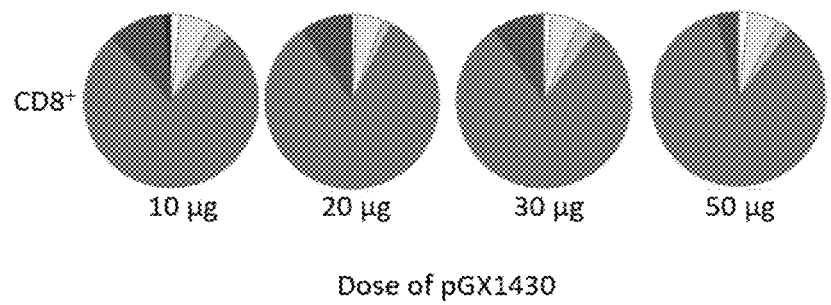

The frequency of antigen specific CD8+ T cells induced by synthetic consensus mesothelin increased over control in all dose groups (FIG. 9B). Specifically, the frequency of antigen specific CD8+ T responses in the groups immunized with 10 μg (0.64%±0.42%) (p=0.016), 20 μg (0.70%±0.48%) (p=0.028), 30 μg (0.97%±0.96%) (p=0.008), and 50 μg (1.00%±0.22%) (p=0.004) of pGX1430 was significantly more robust at the higher doses compared to naïve (0.15%±0.04%). Synthetic consensus mesothelin specific CD8+ T cell responses increased with dose and consisted mainly of IFNγ+IL-2-TNFα-producing CD8+ T cells (FIG. 9D). The frequency of antigen specific CD8+ T cells is further detailed in Table 8.

TABLE 8

Synthetic Consensus Mesothelin CD8+ T cells

| Construct | Dose | % CD8+ ± Std. Dev. | p-value |
|---|---|---|---|
| pGX0001 | 30 μg | 0.15 ± 0.04 | n/a |
| pGX1430 | 10 μg | 0.64 ± 0.42 | 0.016 |
|  | 20 μg | 0.70 ± 0.48 | 0.028 |
|  | 30 μg | 0.97 ± 0.96 | 0.008 |
|  | 50 μg | 1.00 ± 0.22 | 0.004 |

Statistical significance assumed at p ≤ 0.013. p-values reported are relative to naïve (pGX0001 immunized mice).

Figure 10A:
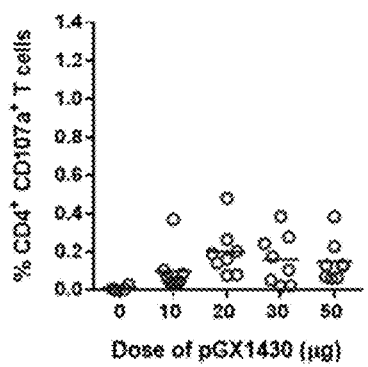
FIGS. 10A-10D illustrate the cytolytic potential of synthetic consensus mesothelin specific T cells.
Figure 10B:
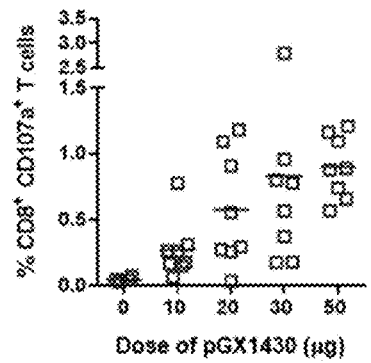
Figure 10C:
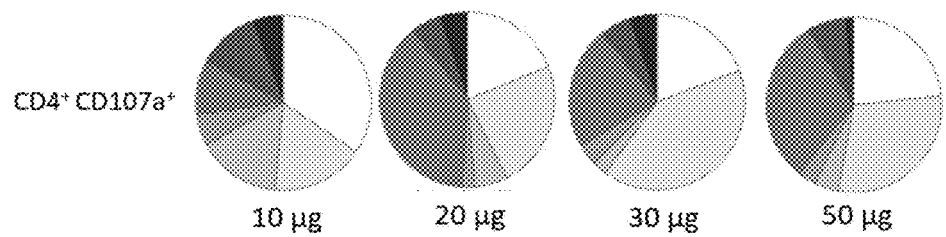

All doses of synthetic consensus mesothelin induced a frequency of CD4+CD107a+ T cells that was greater than naïve (0.01%±0.01%). Specifically, the frequency of antigen specific CD4+CD107a+ T cells was 0.10%±0.11%, 0.20%±0.13%, 0.16%±0.13%, and 0.15%±0.11% in the 10 μg (p=0.004), 20 μg (p=0.004), 30 μg (p=0.016), and 50 μg (p=0.004) dose groups, respectively (FIG. 10A). The cytokine profile of synthetic consensus mesothelin specific CD4+CD107a+ T cells was similar across dose groups and was comprised mainly of IFNγ+IL-2+TNFα+, IFNγ+IL-2+TNFα-, IFNγ+IL-2-TNFα- cells (FIG. 10C). The frequency of antigen specific CD4+ T cells with cytolytic potential is further detailed in Table 9.

TABLE 9

Synthetic Consensus Mesothelin CD4+CD107a+ T cells

| Construct | Dose | % CD4+CD107a+ ± Std. Dev. | p-value |
|---|---|---|---|
| pGX0001 | 30 μg | 0.01 ± 0.01 | n/a |
| pGX1430 | 10 μg | 0.10 ± 0.11 | 0.004 |
|  | 20 μg | 0.20 ± 0.13 | 0.004 |
|  | 30 μg | 0.16 ± 0.13 | 0.016 |
|  | 50 μg | 0.15 ± 0.11 | 0.004 |

Statistical significance assumed at p ≤ 0.013. p-values reported are relative to naïve (pGX0001 immunized mice)

Figure 10D:
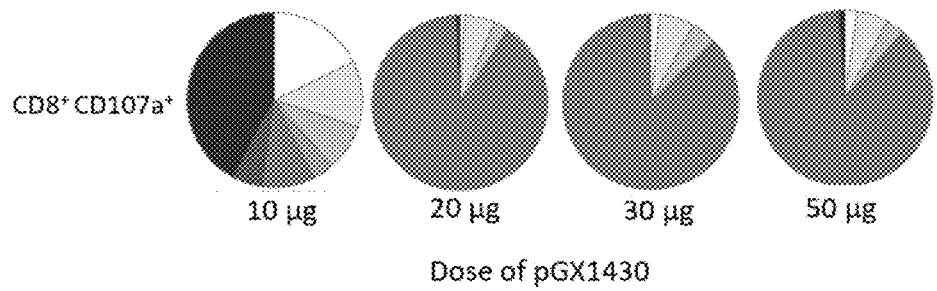

Similar to the magnitude of antigen specific CD8+ T cells, synthetic consensus mesothelin induced a significant change in the frequency of CD8+CD107a+ T cells among all groups compared to naïve (0.05%±0.02%) (FIG. 10C). Specifically, the frequency of antigen specific CD8+CD107a+ T cells was 0.27%±0.22%, 0.57%±0.43%, 0.83%±0.85%, and 0.90%±0.24% in the 10 μg (p=0.008), 20 μg (p=0.028), 30 μg (p=0.004), and 50 μg (p=0.004) dose groups, respectively (FIG. 10A). The cytokine profile of synthetic consensus mesothelin specific CD8+CD107a+ T cells was similar across dose groups and the majority was comprised of IFNγ+IL-2-TNFα- (FIG. 10D) with the exception of the 10 μg dose group where the majority was comprised of IFNγ-IL-2-TNFα+ and IFNγ+IL-2+TNFα+. The frequency of antigen specific CD8+ T cells with cytolytic potential is further detailed in Table 10.

TABLE 10

Synthetic Consensus Mesothelin CD8+CD107a+ T cells

| Construct | Dose | % CD8+CD107a+ ± Std. Dev. | p-value |
|---|---|---|---|
| pGX0001 | 30 μg | 0.05 ± 0.02 | n/a |
| pGX1430 | 10 μg | 0.27 ± 0.22 | 0.008 |
|  | 20 μg | 0.57 ± 0.43 | 0.028 |
|  | 30 μg | 0.83 ± 0.85 | 0.004 |
|  | 50 μg | 0.90 ± 0.24 | 0.004 |

Statistical significance assumed at p ≤ 0.013. p-values reported are relative to naïve (pGX0001 immunized mice)

Overall there were no significant differences in responses between immunized groups for any data reported (i.e. 10 μg was not significantly lower than 50 μg etc.)

Statistical Analysis

Statistical analysis was completed using IBM SPSS Statistics 22 (IBM Corporation). The data was not normally distributed for many comparisons. For this reason, a Mann-Whitney U test was used for all analysis and with a post-hoc Bonferroni correction for multiple comparisons. Statistical significance is assumed at p≤0.013 (0.05/4 comparisons=0.0125).

Conclusion

Synthetic consensus mesothelin increased the frequency of antigen specific CD4+, CD4+CD107a+ and CD8+, CD8+CD107a+ T cells, compared to naïve, although the magnitude of the response was much more robust in the CD8+ T cell compartment.

Example 7: Synthetic Consensus Mesothelin Monovalent Non-Human Primate Study

To investigate the potential of synthetic consensus mesothelin alone and in combination with a low and high dose of IL-12, eighteen adult rhesus monkeys, each identified by a unique NHP ID number, were divided in 3 groups of 6 and immunized with pGX1430 as follows. Six animals were immunized with 3.0 mg pGX1430 (Group 1), six with 3.0 mg pGX1430 plus 0.04 mg of pGX6006 (opt rh IL-12) as an adjuvant (Group 2), and six with 3.0 mg pGX1430 plus 0.20 mg of pGX6006 (opt rh IL-12) as an adjuvant (Group 3), was formulated in SSC in 1.0 mL injection volume. Immunization injections were administered at week 0, 4, 8, and 12, with an optional fifth immunization. All immunizations were carried out IM with CELLECTRA® 2000 5P-IM EP device in a 1 ml injection volume formulated in sterile WFI in alternating contralateral limbs according. The EP conditions were as follows: OpBlock 0070-IM, 0.5 Amp, 3 pulses, 52 msec, 0.2 sec between pulses. Mesothelin immunogenicity was assessed at weeks 2, 6, 10, and 14.

Animal identification, origin, sex and weight for groups 1-3 are provided in Table 11.

TABLE 11

| Group/dose | ID | Origin (if known) | Sex | Weight (kg) |
|---|---|---|---|---|
| 1 | 6864 | Chinese Rhesus | F | 4.5 |
|   | 6870 | Chinese Rhesus | F | 4.0 |
|   | 6876 | Chinese Rhesus | F | 4.1 |
|   | 6882 | Chinese Rhesus | M | 4.0 |
|   | 6889 | Chinese Rhesus | M | 4.4 |
|   | 6896 | Chinese Rhesus | M | 3.9 |
| 2 | 6865 | Chinese Rhesus | F | 4.7 |
|   | 6871 | Chinese Rhesus | F | 4.4 |
|   | 6877 | Chinese Rhesus | F | 4.4 |
|   | 6884 | Chinese Rhesus | M | 4.3 |
|   | 6890 | Chinese Rhesus | M | 3.9 |
|   | 6897 | Chinese Rhesus | M | 3.8 |
| 3 | 6866 | Chinese Rhesus | F | 4.1 |
|   | 6872 | Chinese Rhesus | F | 4.4 |
|   | 6878 | Chinese Rhesus | F | 4.2 |
|   | 6885 | Chinese Rhesus | M | 4.6 |
|   | 6891 | Chinese Rhesus | M | 4.6 |
|   | 6898 | Chinese Rhesus | M | 4.2 |

PBMC Isolation

The Non-Human Primate whole blood was collected in sodium citrate cell preparation tubes (CPT CPT's BD Biosciences) containing an anticoagulant and a gel barrier. Prior to overnight shipment, whole blood is spun shortly after collection (within 2 hours) in order to separate and concentrate PMBC. Red blood cells and neutrophils pellet to the bottom of the tubes and are held in place by a gel barrier. Plasma and lymphocytes remain above the gel barrier. Each CPT can hold ~8 mL of blood and is shipped at room temperature. Upon arrival to the pre-clinical lab in San Diego, the spun CPT tubes were processed for PBMC isolation. After red blood cell lysis with ammonium-chloride-potassium (ACK) buffer, viable cells were counted using Invitrogen Countess™ Automated Cell Counter and resuspended in complete culture medium media (RPMI 1640 supplemented with 10% FBS, antibiotics, and β Mercaptoethanol). Upon completion of assays as described in this report, remaining PBMC were frozen and in freezing media (10% DMSO from Sigma in 90% FBS from Seradigm) in cryovials and stored long term in liquid nitrogen.

IFNγ ELISpot

To evaluate vaccine induced antigen-specific cellular responses, a Monkey IFNγ ELISpot assay was performed at each timepoint, on isolated PMBC using a kit (MabTech IFNγ ELISpotPro, #3421M-2APW-10). In brief, 96 well plates pre-coated with anti-Monkey IFNγ antibody (mAb MT126L) were washed in PBS and blocked for 2 hours at room temperature with complete culture media (RPMI 1640 supplemented with 10% FBS, antibiotics, and β Mercaptoethanol). NHP PBMC were re-suspended in R10 media (and then added in triplicates at an input cell number of 2×105 cells per well. A set of peptides was synthesized (GenScript), each containing 15 amino acid residues overlapping by 11 amino acids representing the entire synthetic consensus protein sequences. These sets of peptides were resuspended in DMSO (Sigma) and pooled at a concentration of approximately 2 μg/mL of each respective peptide, into pools All antigen specific pooled peptides are used at a 1:100 dilution, which results in a final dilution of 1:200 in each well when combined with PBMC. Four pools were generated for Mesothelin.

Anti-CD3 (mAb CD-2 Mabtech) and/or PMA (Sigma) with Ionomycin (Sigma) were used as a positive control. Complete R10 culture medium was used as a negative control. Plates were incubated for approximately 18 hours at 37° C., in a 5% CO2 atmosphere incubator. After cell removal, and addition of an ALP conjugated anti-monkey IFNγ detection antibody (MabTech Ab 7-B6-1-ALP), the plates are incubated for 2 hours at room temperature. The sandwich immune-enzyme assay is then developed using the BCIP/NBT substrate solution according to the kit manufacturer's instructions (MabTech). A blue-black colored precipitate forms as spots to reveal each individual IFNγ producing cell. The spots are then scanned and counted by the CTL ImmunoSpot® Analyzer and Software (Cellular Technology), and quality controlled by a trained operator. The IFNγ responses are reported as Spot Forming Units (SFU) to 1×10$^6$ PMBC greater than the SFU in the media only control.

Immunology Results

Figure 11A:
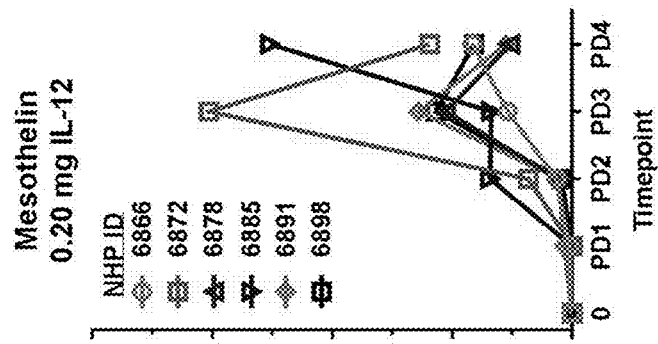
FIGS. 11A-11C show mesothelin-specific IFNγ SFU/10$^6$ PBMCs from individual NHPs using an embodiment of the disclosure.
Figure 11B:
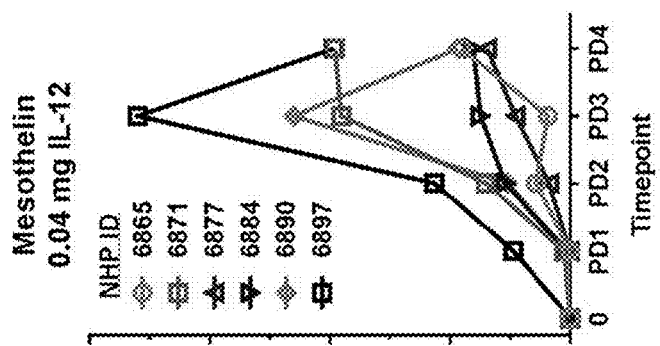
Figure 11C:
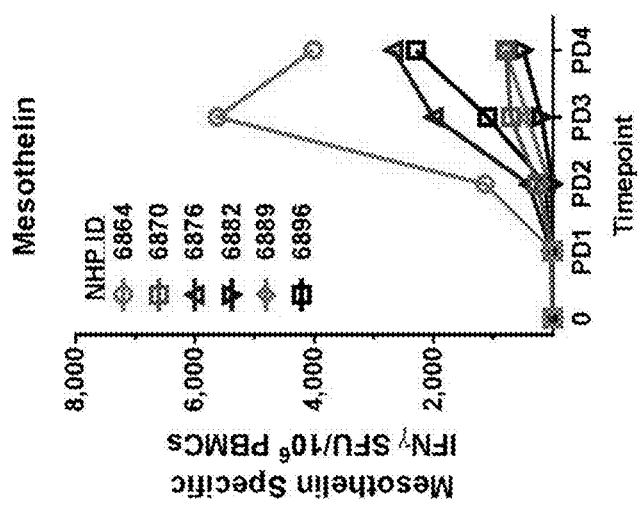

Mesothelin specific IFNγ responses are shown in FIG. 11A-11C for groups 1-3 where immunizations were carried out with mesothelin alone (FIG. 12A), mesothelin with a low dose of IL-12 (0.04 mg) (FIG. 11B), or mesothelin with a high dose of IL-12 (0.2 mg) (FIG. 11C). The results show the response at each time point 2 weeks post dose. Overall, all groups and individual animals had an increase in response by the end of the study at 2 weeks post dose 4 compared to baseline prebleed. FIGS. 11A-11C shows a trend toward IL-12 providing an adjuvant effect for IFNγ responses to synthetic consensus mesothelin through PD3.

Figure 12A:
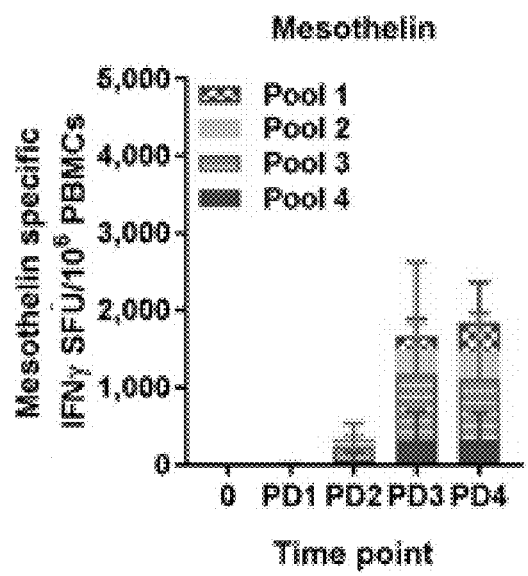
FIG. 12A-12C show averaged mesothelin-specific IFNγ SFU/10$^6$ PBMCs using an embodiment of the disclosure.
Figure 12B:
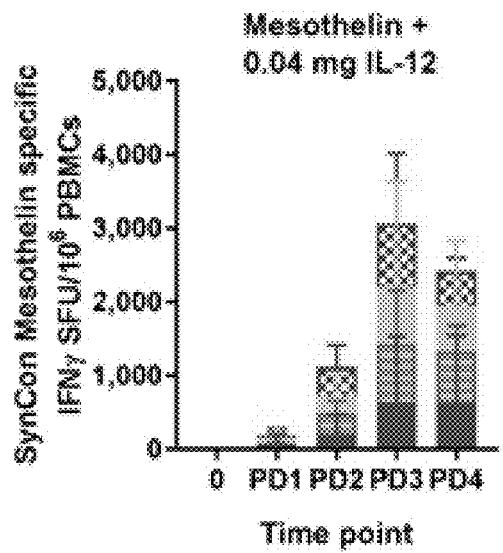
Figure 12C:
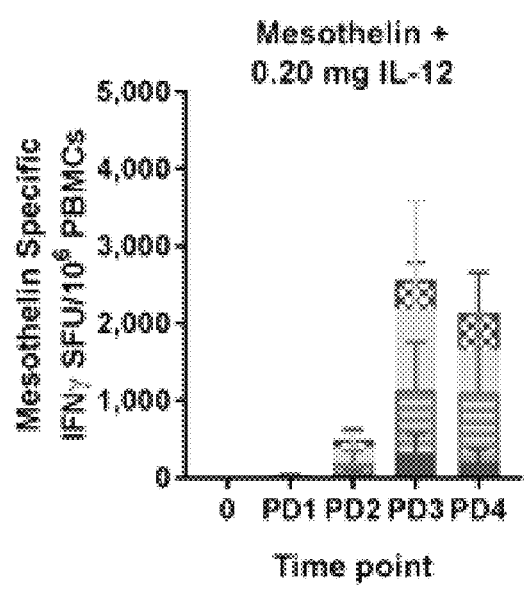

FIGS. 12A-12C depicts averaged mesothelin-specific IFNγ responses, where immunizations were carried out with mesothelin alone (FIG. 12A), mesothelin with a low dose of IL-12 (0.04 mg) (FIG. 12B), or mesothelin with a high dose of IL-12 (0.2 mg) (FIG. 12C). FIGS. 12A-12C show that IL-12 increased magnitude, but not breadth, of IFNγ responses against synthetic consensus mesothelin.

Physiological Parameters

There were no differences in any of the physiological parameters measured due to immunization for groups 1, 2 and 3 as shows in Tables 12, 13 and 14, respectively. No significant differences were noted for RBCs, HCTs, neutrophils, lymphocytes, monocytes, eosinophils (data not shown). These values are within the expected ranges for animals of this species, gender, and age undergoing similar experimental procedures. Any variations from stated normal ranges are of a sporadic nature, present in only one gender, and are not related to dose levels or timing.

TABLE 12

| | Pre-Vaccination | Post-Vaccination | | Normal |
|---|---|---|---|---|
| Group 1 | Week −2 | Week 6 | Week 14 | Range |
| WBC Count (#/10$^3$/ml) | 3.4*-11.9 (#6896, 6882) | 3.3*-9.5 (#6896, 6882) | 3.4*-12.6 (#6896, 6882) | 4.0-15.0 |
| Creatinine (mg/dL) | 0.5-0.9 | 0.4-0.9 | 0.5-0.9 | 0.3-1.4 |
| BUN (mg/dL) | 9-23 | 14-27 | 11-28 | 9-29 |
| ALK P (U/L) | 197-576 | 238-551 | 218-673 | 65-641 |
| AST (U/L) | 9*-23 (#6889, 6870, 6882) | 7*-26 (#6889, 6870, 6882, 6864) | 20*-44 (#6870) | 23-175 |
| ALT (U/L) | 19-40 | 12*-28 (#6870) | 8*-30 (#6889) | 18-204 |
| TBIL (mg/dL) | 0.1-0.2 | 0.2-0.3 | 0.1-0.3 | 0.1-0.6 |

Note:
Outside of normal range*

TABLE 13

| Group 2 | Pre-Vaccination Week −2 | Post-Vaccination Week 6 | Post-Vaccination Week 14 | Normal Range |
|---|---|---|---|---|
| WBC Count (#/10³/ml) | 5.9-16.2 | 5.1-9.2 | 7.1-11.9 | 4.0-15.0 |
| Creatinine (mg/dL) | 0.5-0.8 | 0.4-0.8 | 0.4-0.9 | 0.3-1.4 |
| BUN (mg/dL) | 11-18 | 13-19 | 14-19 | 9-29 |
| ALK P (U/L) | 256-419 | 331-435 | 324-490 | 65-641 |
| AST (U/L) | 14*-29 (#6871, 6865, 6897, 6877) | 15*-34 (#6871, 6865, 6897, 6877) | 21*-34 (#6865) | 23-175 |
| ALT (U/L) | 17*-43 (#6865) | 17*-34 (#6865) | 18-40 | 18-204 |
| TBIL (mg/dL) | 0.2 | 0.2-0.3 | 0.2-0.4 | 0.1-0.6 |

Note:
Outside of normal range*

TABLE 14

| Group 3 | Pre-Vaccination Week −2 | Post-Vaccination Week 6 | Post-Vaccination Week 14 | Normal Range |
|---|---|---|---|---|
| WBC Count (#/10³/ml) | 5.3-13.7 | 3.8*-11.0 (#6885) | 3.9*-16.5 (#6885) | 4.0-15.0 |
| Creatinine (mg/dL) | 0.5-0.7 | 0.5-0.7 | 0.6-0.8 | 0.3-1.4 |
| BUN (mg/dL) | 11-21 | 13-22 | 12-25 | 9-29 |
| ALK P (U/L) | 302-405 | 363-441 | 332-439 | 65-641 |
| AST (U/L) | 8*-31 (#6891, 6878, 6898) | 6*-32 (#6891, 6898, 6872, 6885) | 21*-43 (#6885, 6891) | 23-175 |
| ALT (U/L) | 15*-34 (#6878) | 15*-36 (#6885) | 8*-33 (#6891) | 18-204 |
| TBIL (mg/dL) | 0.1-0.2 | 0.1-0.2 | 0.1-0.2 | 0.1-0.6 |

Note:
Outside of normal range*

For all Groups, there was no significant change in weight over the course of the study, where the normal range is 4-12, as shown below in Table 15.

TABLE 15

| Groups | Weight (kg) Month 1 | Month 2 | Month 3 | Month 4 | Month 5 |
|---|---|---|---|---|---|
| 4 | 4.12-5.38 | 3.94*-5.48 (#6882) | 3.88*-5.56 (#6882) | 4.0-5.9 | 3.94*-5.84 (#6882) |
| 5 | 4.14-5.26 | 3.92*-5.34 (#6897) | 3.88*-5.46 (#6897) | 3.94*-5.24 (#6897) | 3.88*-5.38 (#6897) |
| 6 | 4.68-5.28 | 4.54-5.36 | 4.56-5.32 | 4.82-5.8 | 4.72-5.74 |

Overall the results indicate that synthetic consensus mesothelin administered alone are capable of inducing an immune response in 100% of NHPs. There was not a significant improvement with the addition of IL-12 adjuvant.

It is understood that the foregoing detailed description and accompanying examples are merely illustrative and are not to be taken as limitations upon the scope of the invention, which is defined solely by the appended claims and their equivalents.

Various changes and modifications to the disclosed embodiments will be apparent to those skilled in the art. Such changes and modification to the disclosed embodiments, including without limitation those relating to the chemical structures, substituents, derivatives, intermediates, syntheses, compositions, formulations, or methods of use of the invention, may be made without departing from the spirit and scope thereof.

TABLE 1

Synthetic Consensus Mesothelin DNA Coding Sequence

| SEQ ID NO. | SEQUENCE |
|---|---|
| 1 | ATGGACTGGACATGGATTCTGTTTCTGGTCGCCGCCGCTACACGAGTGCATTCAAGCAGGGCTCTGGCAGGGGAGACTGGGCAGGAAGCAGCCCCACTGGACGGCGTGCTGGCAAACCCTCCCGATATCAGCTCCCTGAGCCCTAGACAGCTGCTGGGCTTCCCATGCGTGGAGGTGAGCGGCCTGTCCACCGAGAGGGTGCGCGAGCTGGCAGTGGCCCTGGCACAGAAGAATGTGAAGCTGTCCGCCGAGCAGCTGAGGTGCCTGGCACACAGGCTGTCTGAGCCACCCGAGGACCTGGATGCACTGCCACTGGACCTGCTGCTGTTCCTGAACCCCGATGCCTTTAGCGGCCCTCAGGCCTGTACAAGGTTCTTTTCCCGCGTGGCCAAGGCCAATGTGGACCTGCTGCCTAGGGGCGCCCCAGAGCGGCAGAGACTGCTGCCAGCCGCCCTGGCATGCTGGGCGTGAGGGGCTCTCTGCTGAGCGAGGCAGACGTGCGCGCCCTGGGCGGCCTGGCCTGTGATCTGCCTGGCCGCTTTGTGGCCGAGTCTGCCGAGGTGCTGCTGCCAAGGCTGGTGAGCTGCCTGGGACCTCTGGACCAGGATCAGCAGGAGGCCGTGCGCGCCGCCCTGCAGGGCGGCGGCCCTCCCTACGCCCTCCCTCTACCTGGTCTATCAGCACACTGGACGCACTGAGAGGCAGCCTGCCAGTGCTGGGACAGCCCGTGATCAGGTCCATCCCTCAGGGCATCCTGGCAGCATGGAGGCAGCGGAGCAGCCGGGACCCCTCCTGGAGGCAGCCAGAGAGAACCGTGCTGAGGCCTAGATTCCGGAGAGACGTGGAGAAGACAGCCTGTCCATCCGGCAAGAAGGTGCACGAGATCGATGAGTCTCTGATCTTTGCCAAGAAGTGGGAGCTGGAGGCATGCGTGGACGCCGCCCTGCTGGCAGCACAGATGGATAGAGTGAACGCCATCCCCTTCACCTACGAGCAGCTGGACGTGCTGAAGCACAAGCTGGATGAGCTGTACCCCCAGGGCTATCCTGAGAGCGTGACACAGCACCTGGGCTATCTGTTTCTGAAGATGTCTCCTGAGGACATCAGGAAGTGGAACGTGACCAGCCTGGAGACACTGAAGGCCCTGCTGGAGGTCAATAAGGGCCACGAGATGTCCCCACAGGTGGCCACCCTGATCGACAGGGTGGTGAAGGGCAGAGGCCAGCTGGACAAGGATACAGTGGATACCCTGACAGCCTTCTACCCAGGCTACCTGTGCTCCCTGTCTCCCGAGGAGCTGTCCTCTGTGCCACCCAGCTCCATCGGAGCCGTGCGGCCTCAGGACCTGGATACCTGCGACCCAAGACAGCTGGATGTGCTGTACCCCAAGGCCAGGCTGGCCTTCCAGAACATGAATGGCAGCGAGTATTTCGTGAAGATCCAGCCATTTCTGGGCGGCGCCCAACCGAGGACCTGAAGGCCCTGTCCCAGCAGAACGTGTCTATGGACCTGGCCACCTTTATGAAGCTGCGCACAGATGCCGTGCTGCCACTGACAGTGGCAGAGGTGCAGAAGCTGCTGGGACCTCACGTGGAGGG |

TABLE 1-continued

| Synthetic Consensus Mesothelin DNA Coding Sequence | |
|---|---|
| SEQ ID NO. | SEQUENCE |
| | CCTGAAGGCAGAGGAGAGGCACAGG CCCGTGCGGGACTGGATTCTGCGGC AGAGACAGGACGATCTGGATACCCT GGGACTGGGACTGCAGGGCGGCATC CCAAATGGCTATCTGGTGCTGGATC TGTCCGTGCGGGAGGCCCTGACAGG CGTGCCCTGCCTGCTGGGACCTGGA CCTGTGCTGACTGTGCTGGCTCTGC TGCTGGCTTCAACACTGGCTTGATA A |

TABLE 17

| Synthetic Consensus Mesothelin Protein Sequence | |
|---|---|
| SEQ ID NO. | SEQUENCE |
| 2 | MDWTWILFLVAAATRVHSSRALAGET GQEAAPLDGVLANPPDISSLSPRQL LGFPCVEVSGLSTERVRELAVALAQ KNVKLSAEQLRCLAHRLSEPPEDLD ALPLDLLLFLNPDAFSGPQACTRFF SRVAKANVDLLPRGAPERQRLLPAA LACWGVRGSLLSEADVRALGGLACD LPGRFVAESAEVLLPRLVSCLGPLD QDQQEAVRAALQGGGPPYGPPSTWS ISTLDALRGSLPVLGQPVIRSIPQG ILAAWRQRSSRDPSWRQPERTVLRP RFRRDVEKTACPSGKKVHEIDESLI FAKKWELEACVDAALLAAQMDRVNA IPFTYEQLDVLKHKLDELYPQGYPE SVTQHLGYLFLKMSPEDIRKWNVTS LETLKALLEVNKGHEMSPQVATLID RVVKGRGQLDKDTVDTLTAFYPGYL CSLSPEELSSVPPSSIGAVRPQDLD TCDPRQLDVLYPKARLAFQNMNGSE YFVKIQPFLGGAPTEDLKALSQQNV SMDLATFMKLRTDAVLPLTVAEVQK LLGPHVEGLKAEERHRPVRDWILRQ RQDDLDTLGLGLQGGIPNGYLVLDL SVREALTGVPCLLGPGPVLTVLALL LASTLA |

What is claimed is:

1. A protein comprising the amino acid sequence selected from the group consisting of:
   (a) amino acids 19-607 of SEQ ID NO: 2;
   (b) an amino acid sequence that is at least 96% identical to amino acids 19-607 of SEQ ID NO: 2, wherein the protein comprises an alanine at amino acid position 303, a threonine at amino acid position 583, and a valine at amino acid position 585 relative to SEQ ID NO: 2.

2. A protein comprising the amino acid sequence selected from the group consisting of:
   (a) SEQ ID NO: 2;
   (b) an amino acid sequence that is at least 96% identical to SEQ ID NO: 2, wherein the protein comprises an alanine at amino acid position 303, a threonine at amino acid position 583, and a valine at amino acid position 585 relative to SEQ ID NO: 2.

3. A protein comprising the amino acid sequence set forth in SEQ ID NO: 2.

* * * * *

SEQUENCE LISTING

<160> NUMBER OF SEQ ID NOS: 2

<210> SEQ ID NO 1
<211> LENGTH: 1827
<212> TYPE: DNA
<213> ORGANISM: Artificial Sequence
<220> FEATURE:
<223> OTHER INFORMATION: Synthetic Consensus Mesothelin DNA Coding Sequence

<400> SEQUENCE: 1

```
atggactgga catggattct gtttctggtc gccgccgcta cacgagtgca ttcaagcagg     60
gctctggcag gggagactgg gcaggaagca gccccactgg acggcgtgct ggcaaaccct    120
cccgatatca gctccctgag ccctagacag ctgctgggct tcccatgcgt ggaggtgagc    180
ggcctgtcca ccgagagggt gcgcgagctg gcagtggccc tggcacagaa gaatgtgaag    240
ctgtccgccg agcagctgag gtgcctggca cacaggctgt ctgagccacc cgaggacctg    300
gatgcactgc cactggacct gctgctgttc ctgaaccccg atgcctttag cggccctcag    360
gcctgtacaa ggttcttttc ccgcgtggcc aaggccaatg tggacctgct gcctaggggc    420
gccccagagc ggcagagact gctgccagcc gccctggcat gctggggcgt gaggggctct    480
ctgctgagcg aggcagacgt gcgcgccctg ggcggcctgg cctgtgatct gcctggccgc    540
tttgtggccg agtctgccga ggtgctgctg ccaaggctgg tgagctgcct gggacctctg    600
gaccaggatc agcaggaggc cgtgcgcgcc gccctgcagg gcggcggccc tccctacggc    660
cctccctcta cctggtctat cagcacactg gacgcactga gaggcagcct gccagtgctg    720
ggacagcccg tgatcaggtc catccctcag ggcatcctgg cagcatggag gcagcggagc    780
agccgggacc cctcctggag gcagccagag agaaccgtgc tgaggcctag attccggaga    840
gacgtggaga agacagcctg tccatccggc aagaaggtgc acgagatcga tgagtctctg    900
```

```
atctttgcca agaagtggga gctggaggca tgcgtggacg ccgccctgct ggcagcacag    960
atggatagag tgaacgccat ccccttcacc tacgagcagc tggacgtgct gaagcacaag   1020
ctggatgagc tgtaccccca gggctatcct gagagcgtga cacagcacct gggctatctg   1080
tttctgaaga tgtctcctga ggacatcagg aagtggaacg tgaccagcct ggagacactg   1140
aaggccctgc tggaggtcaa taagggccac gagatgtccc cacaggtggc caccctgatc   1200
gacagggtgg tgaagggcag aggccagctg acaaggata cagtggatac cctgacagcc   1260
ttctacccag gctacctgtg ctccctgtct cccgaggagc tgtcctctgt gccacccagc   1320
tccatcggag ccgtgcggcc tcaggacctg gatacctgcg acccaagaca gctggatgtg   1380
ctgtacccca aggccaggct ggccttccag aacatgaatg gcagcgagta tttcgtgaag   1440
atccagccat ttctgggcgg cgccccaacc gaggacctga aggccctgtc ccagcagaac   1500
gtgtctatgg acctggccac ctttatgaag ctgcgcacag atgccgtgct gccactgaca   1560
gtggcagagg tgcagaagct gctgggacct cacgtggagg gcctgaaggc agaggagagg   1620
cacaggcccg tgcgggactg gattctgcgg cagagacagg acgatctgga taccctggga   1680
ctgggactgc agggcggcat cccaaatggc tatctggtgc tggatctgtc cgtgcgggag   1740
gccctgacag gcgtgccctg cctgctggga cctggacctg tgctgactgt gctggctctg   1800
ctgctggctt caacactggc ttgataa                                       1827
```

```
<210> SEQ ID NO 2
<211> LENGTH: 607
<212> TYPE: PRT
<213> ORGANISM: Artificial Sequence
<220> FEATURE:
<223> OTHER INFORMATION: Synthetic Consensus Mesothelin Protein Sequence

<400> SEQUENCE: 2

Met Asp Trp Thr Trp Ile Leu Phe Leu Val Ala Ala Thr Arg Val
1               5                   10                  15

His Ser Ser Arg Ala Leu Ala Gly Glu Thr Gly Gln Glu Ala Pro
            20                  25                  30

Leu Asp Gly Val Leu Ala Asn Pro Pro Asp Ile Ser Ser Leu Ser Pro
        35                  40                      45

Arg Gln Leu Leu Gly Phe Pro Cys Val Glu Val Ser Gly Leu Ser Thr
    50                  55                      60

Glu Arg Val Arg Glu Leu Ala Val Ala Leu Ala Gln Lys Asn Val Lys
65                  70                      75                  80

Leu Ser Ala Glu Gln Leu Arg Cys Leu Ala His Arg Leu Ser Glu Pro
                85                  90                  95

Pro Glu Asp Leu Asp Ala Leu Pro Leu Asp Leu Leu Leu Phe Leu Asn
            100                 105                 110

Pro Asp Ala Phe Ser Gly Pro Gln Ala Cys Thr Arg Phe Phe Ser Arg
        115                 120                 125

Val Ala Lys Ala Asn Val Asp Leu Leu Pro Arg Gly Ala Pro Glu Arg
    130                 135                 140

Gln Arg Leu Leu Pro Ala Ala Leu Ala Cys Trp Gly Val Arg Gly Ser
145                 150                 155                 160

Leu Leu Ser Glu Ala Asp Val Arg Ala Leu Gly Gly Leu Ala Cys Asp
                165                 170                 175

Leu Pro Gly Arg Phe Val Ala Glu Ser Ala Glu Val Leu Leu Pro Arg
            180                 185                 190

Leu Val Ser Cys Leu Gly Pro Leu Asp Gln Asp Gln Gln Glu Ala Val
```

```
            195                 200                 205
Arg Ala Ala Leu Gln Gly Gly Pro Pro Tyr Gly Pro Pro Ser Thr
210                 215                 220

Trp Ser Ile Ser Thr Leu Asp Ala Leu Arg Gly Ser Leu Pro Val Leu
225                 230                 235                 240

Gly Gln Pro Val Ile Arg Ser Ile Pro Gln Gly Ile Leu Ala Ala Trp
                245                 250                 255

Arg Gln Arg Ser Ser Arg Asp Pro Ser Trp Arg Gln Pro Glu Arg Thr
            260                 265                 270

Val Leu Arg Pro Arg Phe Arg Arg Asp Val Glu Lys Thr Ala Cys Pro
        275                 280                 285

Ser Gly Lys Lys Val His Glu Ile Asp Glu Ser Leu Ile Phe Ala Lys
    290                 295                 300

Lys Trp Glu Leu Glu Ala Cys Val Asp Ala Ala Leu Leu Ala Ala Gln
305                 310                 315                 320

Met Asp Arg Val Asn Ala Ile Pro Phe Thr Tyr Glu Gln Leu Asp Val
                325                 330                 335

Leu Lys His Lys Leu Asp Glu Leu Tyr Pro Gln Gly Tyr Pro Glu Ser
            340                 345                 350

Val Thr Gln His Leu Gly Tyr Leu Phe Leu Lys Met Ser Pro Glu Asp
        355                 360                 365

Ile Arg Lys Trp Asn Val Thr Ser Leu Glu Thr Leu Lys Ala Leu Leu
    370                 375                 380

Glu Val Asn Lys Gly His Glu Met Ser Pro Gln Val Ala Thr Leu Ile
385                 390                 395                 400

Asp Arg Val Val Lys Gly Arg Gly Gln Leu Asp Lys Asp Thr Val Asp
                405                 410                 415

Thr Leu Thr Ala Phe Tyr Pro Gly Tyr Leu Cys Ser Leu Ser Pro Glu
            420                 425                 430

Glu Leu Ser Ser Val Pro Pro Ser Ile Gly Ala Val Arg Pro Gln
        435                 440                 445

Asp Leu Asp Thr Cys Asp Pro Arg Gln Leu Asp Val Leu Tyr Pro Lys
    450                 455                 460

Ala Arg Leu Ala Phe Gln Asn Met Asn Gly Ser Glu Tyr Phe Val Lys
465                 470                 475                 480

Ile Gln Pro Phe Leu Gly Gly Ala Pro Thr Glu Asp Leu Lys Ala Leu
                485                 490                 495

Ser Gln Gln Asn Val Ser Met Asp Leu Ala Thr Phe Met Lys Leu Arg
            500                 505                 510

Thr Asp Ala Val Leu Pro Leu Thr Val Ala Glu Val Gln Lys Leu Leu
        515                 520                 525

Gly Pro His Val Glu Gly Leu Lys Ala Glu Arg His Arg Pro Val
    530                 535                 540

Arg Asp Trp Ile Leu Arg Gln Arg Gln Asp Leu Asp Thr Leu Gly
545                 550                 555                 560

Leu Gly Leu Gln Gly Gly Ile Pro Asn Gly Tyr Leu Val Leu Asp Leu
                565                 570                 575

Ser Val Arg Glu Ala Leu Thr Gly Val Pro Cys Leu Leu Gly Pro Gly
            580                 585                 590

Pro Val Leu Thr Val Leu Ala Leu Leu Ala Ser Thr Leu Ala
        595                 600                 605
```